(12) United States Patent
Anderson et al.

(10) Patent No.: US 12,193,584 B2
(45) Date of Patent: Jan. 14, 2025

(54) SYSTEMS AND METHODS FOR SECURE PACKAGE DELIVERY AND RETRIEVAL

(71) Applicants: Jerry Anderson, Lago Vista, TX (US); Jay Houser, Argyle, TX (US); Guy Chaney, Seminole, TX (US)

(72) Inventors: Jerry Anderson, Lago Vista, TX (US); Jay Houser, Argyle, TX (US); Guy Chaney, Seminole, TX (US)

( * ) Notice: Subject to any disclaimer, the term of this patent is extended or adjusted under 35 U.S.C. 154(b) by 113 days.

(21) Appl. No.: 18/120,722

(22) Filed: Mar. 13, 2023

(65) Prior Publication Data

US 2023/0210295 A1   Jul. 6, 2023

Related U.S. Application Data

(63) Continuation-in-part of application No. 16/934,408, filed on Jul. 21, 2020, now Pat. No. 11,602,236.

(60) Provisional application No. 62/876,912, filed on Jul. 22, 2019.

(51) Int. Cl.
  *A47G 29/14* (2006.01)
  *A61L 2/10* (2006.01)
  *F24S 20/60* (2018.01)
  *H04N 7/18* (2006.01)

(52) U.S. Cl.
  CPC ............ *A47G 29/141* (2013.01); *A61L 2/10* (2013.01); *F24S 20/60* (2018.05); *H04N 7/181* (2013.01); *A47G 2029/144* (2013.01); *A47G 2029/145* (2013.01); *A47G 2029/147* (2013.01); *A47G 2029/149* (2013.01); *A61L 2202/11* (2013.01); *A61L 2202/23* (2013.01)

(58) Field of Classification Search
  None
  See application file for complete search history.

(56) References Cited

U.S. PATENT DOCUMENTS 11,602,236 B2 *  3/2023  Anderson .......... G06Q 10/0832

FOREIGN PATENT DOCUMENTS

WO      WO2001097664 A    12/2001

* cited by examiner

*Primary Examiner* — K. Wong
(74) *Attorney, Agent, or Firm* — Kirby Drake

(57) ABSTRACT

Systems and methods for smooth attended or unattended package delivery and retrieval may be provided through a container locker. Delivery companies and their respective delivery means may interact with the container locker wirelessly, through handheld devices, or through mechanisms provided on the container locker itself. The processes of receiving or pickup of a parcel or other item may be facilitated, regardless the user's presence or absence from the delivery/pickup location. Systems and methods may receive, secure, maintain, and temporarily house delivery or pickup items and concomitantly document, verify, confirm, and communicate data in varied forms to the parties interested or engaged in such deliveries or retrievals through a variety of connected networks, communication means and the use thereof.

20 Claims, 9 Drawing Sheets

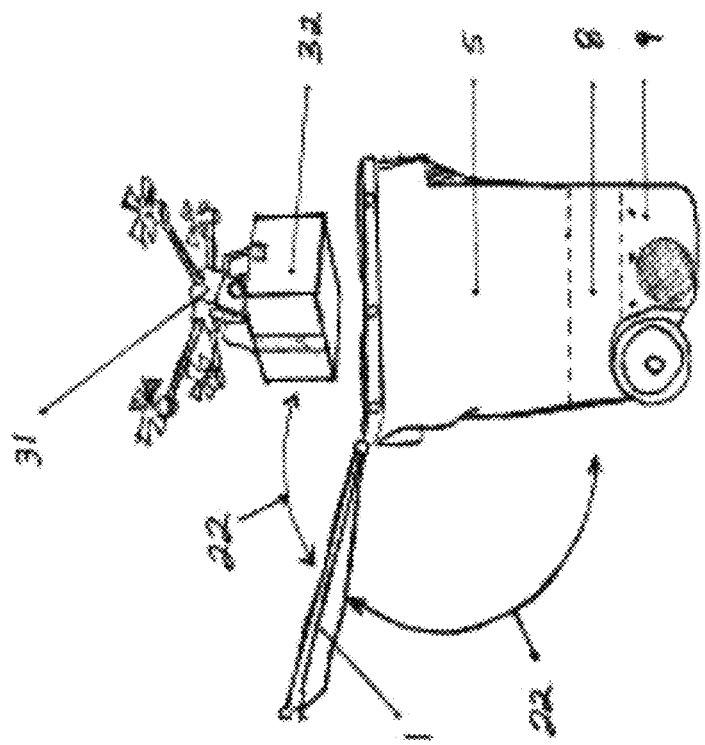

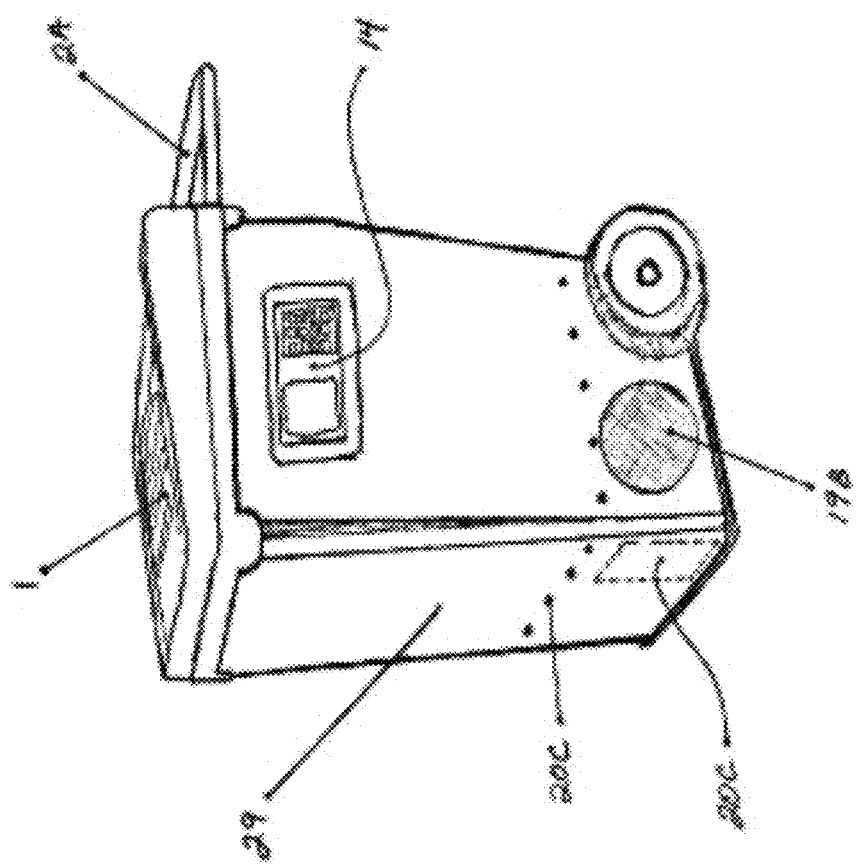

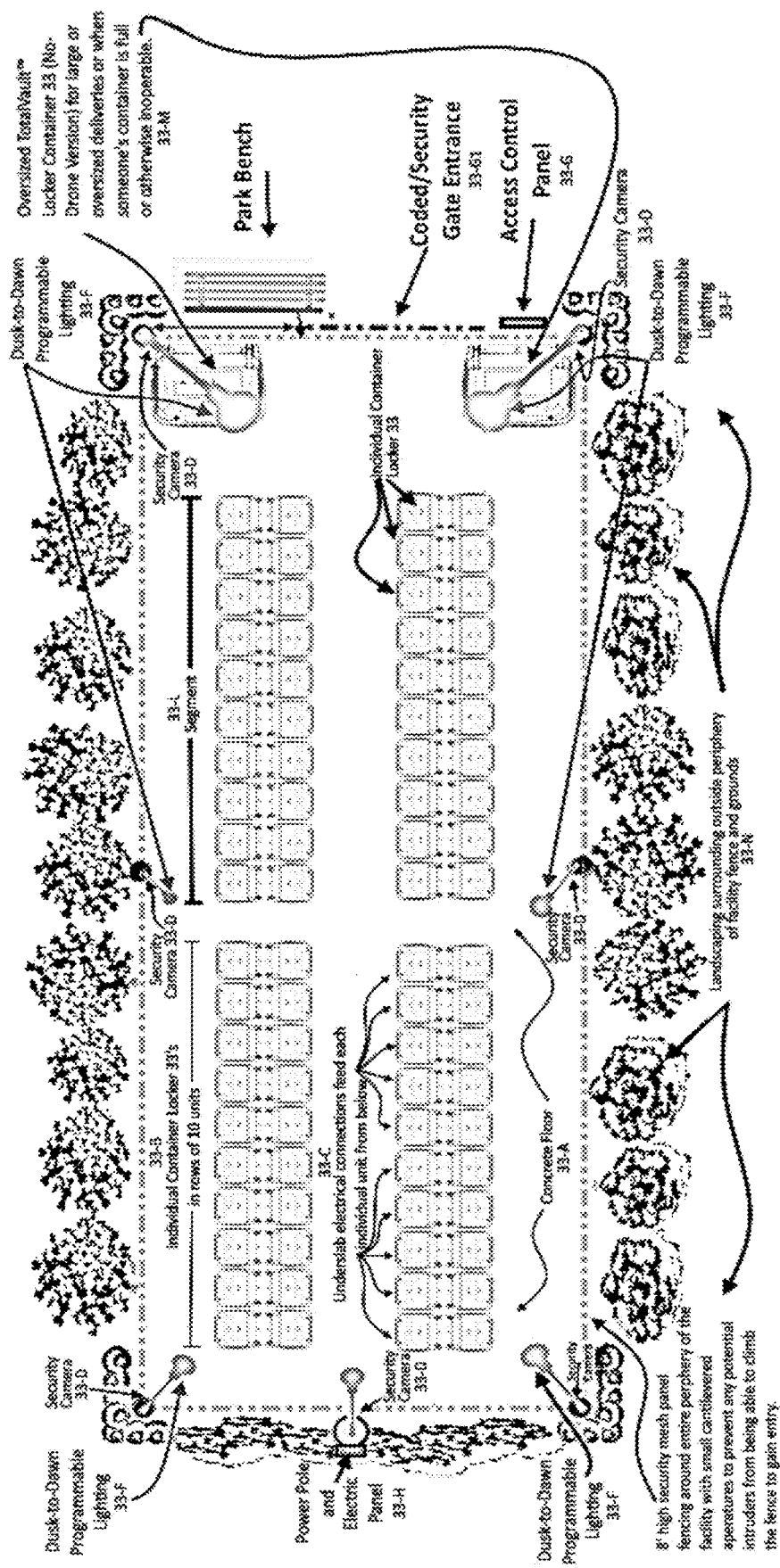

SYSTEMS AND METHODS FOR SECURE PACKAGE DELIVERY AND RETRIEVAL

CROSS REFERENCE TO RELATED APPLICATIONS

This application is a continuation-in-part of U.S. patent application Ser. No. 16/934,408 filed Jul. 21, 2020 which claims the benefit under 35 U.S.C. § 119(e) of U.S. Provisional Patent Application Ser. No. 62/876,912 filed on Jul. 22, 2019, entitled "SYSTEM, DEVICES AND METHOD TO PROVIDE THE SECURED AUTOMATED MODULAR & PORTABLE ENVIRONMENTALLY/TEMPERATURE-CONTROLLED LOCKER CONTAINER FOR THE TEMPORARY STORAGE OF ITEMS AND FOR MANNED OR UNMANNED DELIVERY OR RETRIEVAL WITH MECHANICAL AND DIGITAL SECURITY, VISUAL, AUDIBLE AND DATA RECORDATION AND COMMUNICATION CAPABILITIES AND OTHER UTILITY AND FEATURES," each of which is incorporated by reference in its entirety.

FIELD OF THE DISCLOSURE

The present disclosure generally relates to package delivery and retrieval, and more particularly to systems and methods to protect the packages and verify that the delivery or retrieval event has occurred.

BACKGROUND

When a retailer, vendor, supplier or other purveyor of goods delivers a parcel, package, bag or loose item to a purchaser, there is an agreement made between the buyer and the seller of the item(s) purchased. Typically, where delivery to a buyer is a part of the bargain, the purchaser of the item(s) has either made payment on his/her credit card, the seller has already been paid for the item and, outside of warranty or agreed return of item issues, successful delivery to the buyer retires the obligation to deliver the item to the buyer once the item has been placed in, on, or nearby the purchaser's domicile front door, office doorway or other mutually agreeable location. For a third-party delivery person and/or her/his company, it is likely that she/he is engaged in a bailment activity or performance, wherein the transfer of possession of an item has occurred when she/he actually performs (completes) the delivery or retrieval. If something goes wrong, who is at fault? This question introduces multiple points of risk to the delivery/pickup equation that can subject the delivered item to a wide range of issues while the item sits and waits on its intended recipient to retrieve it. Obviously, theft and/or spoilage is a consideration. What if the delivery person places the delivery at the foot of the intended recipient's front house door and another passerby (porch pirate) confiscates it before the intended recipient arrives? What if it is 100 degrees today and the package was left in the sun? As one can see, delivery and pickups (returns of goods) can be quite complicated, and there are a lot of places for the introduction of risk, miscommunication, and misunderstanding in these processes, given all of the separate parties that perform their work therein, to take hold in the overall process of getting a good from a seller's operation or warehouse to the purchaser.

In addition to the costs associated with performing delivery and/or retrieval tasks, the existence of these legal complications is part and parcel, no pun intended, to what makes "the Last Mile Conundrum" an actual conundrum in the first place. One of the biggest roadblocks people and online merchandisers and other purveyors of goods face daily is the seamless conveyance of the item ordered (and usually paid for) to the purchaser. That is, getting the item to the person that bought it. When these people buying goods online attempt to have their purchases and other items delivered and or picked up from or at their location, they are faced with having to provide a safe, locked down and secured and/or climate controlled environment to store the item(s) temporarily until their delivery or return, regardless how it is achieved. Holistically, we refer to this as the Last Mile Conundrum," that is, the last part of the distance between seller and purchaser in a delivery: getting the purchased good(s) physically to the buyer/recipient safely, securely and dutifully and confirming that the task is completed. "The last mile" is, holistically, everything involved in the delivery or retrieval given the distance, the people, timing variances, and other uncompromising aspects that commonly exist between the location of the good when purchased (its origin) and its final destination. Actually being able to leave the delivery or pick up the item to be transported elsewhere as a return at or from that location if one of the parties is absent presents an altogether different set of problems, especially when intended recipient is unable to be present for the act to occur in person. Studies have shown that 74% of packages are stolen from homes during the day when homeowners are at work, and the rate of package theft has been steadily increasing. More than 1.7 million packages are stolen or go missing daily, adding up to $25 million USD in lost goods and services and costing sellers around $9 billion each year. And demand for devices and systems that accommodate the phenomenon of "everything being delivered to your door" are growing by leaps and bounds. Further, same-day delivery is becoming more critical.

SUMMARY

Embodiments of the present disclosure may provide highly secured and coded accessibility through container lockers which may be capable of use by either manned or unmanned parties for access provided that such man or machine accessing the container locker is a permitted invitee thereof. This container locker may serve as a storage or holding cavity designed for receiving multiple deliveries to be made into it. For outbound items being returned to the purveyor, the device securely holds the item(s) until they are able to be retrieved by the appropriate collector thereof. The container locker may include at least one locking door or hatch or multiple or several locking doors/hatches to secure goods or items. These access points provide coded, bio-coded, or keyed access to its additional interior sub-domains (holding areas) by authorized persons and deter and prevent others without permission to access it from gaining entry. In some embodiments, the container locker may be controlled remotely via an App operating through a cell phone or computer which may also permit the user to relocate (drive) the container locker to a more secure predesignated GPS location or visually (using cameras) determined location. The container locker's on-board electronic security systems may enable it to be secured and alarmed electronically, digitally, and/or otherwise mechanically, and/or, in other embodiments, it may provide simple lock and key containment. Controlled heated and/or refrigerated storage for contents placed therein may be provided and can serve the automated delivery of a parcel or item(s) by manned delivery personnel, a remotely-controlled unmanned aerial vehicle (UAV) and/or other manned or unmanned deliveries, such as automated remotely-controlled delivery non-aerial vehicle or apparatus to a receiver/recipient in a secured manner in their absence. This system also may allow for electronically dated (date-stamped), weighed, and time-stamped communication between the deliverer, the sender, the recipient, and other interested parties, so they may be electronically alerted to the conveyance or delivery status of the parcel or item(s), and users may be electronically notified and made aware of confirmation that such parcel or item(s) has been delivered or picked up securely to or from the container locker. In addition to using GPS to confirm where, geographically, such container locker may be physically located at any specific point in time of its use, systems and methods according to embodiments of the present disclosure can also provide wireless transmission of other pertinent data and information to parties interested in the delivery or pickup. This system and method may provide a communicative wirelessly or hard-wire connected "smart-receptacle" for deliveries and may receive multiple deliveries of multiple types and sizes with varied delivery requirements from multiple senders thereof in any given day or period of time.

Embodiments of the present disclosure may provide a container locker comprising: a first cavity that accepts or holds one or more parcels; a second cavity positioned below the first cavity, the second cavity having a ceiling that provides a cushioned surface for the first cavity to receive the one or more parcels, a scale, and a scale deck to weigh the one or more parcels; a third cavity that houses mechanical and electrical equipment for operation of the container locker; and a lockable lid that removably covers the first cavity. The second cavity may further include a drop-cushion spring system positioned below the ceiling. The mechanical and electrical equipment in the interior or exterior, preferably in the third cavity, in whole or in part, may comprise one or more of the following: refrigeration equipment, heating/warming equipment, cellular phones and related cellular technology communication and interface devices, on-board single board computers and other computers and interface devices, 4G, 5G (and future versions of these protocols) repeater(s) or relay modules to complete 4G 5G (including contemplated future versions thereof) networks and communication systems, interior and exterior cameras, scanners and optical devices, USB and other computer interface connection ports, Wi-Fi repeaters and boosters, antennas and transmitter and transceiving devices, communication and uplink modules, equipment and devices, electrical cords and plugs and related powering and charging equipment, batteries, battery-well access hatches and locks, security cords, power cords, gyroscopic devices, motion sensors, speakers, horns, piezoelectric sounders, interior or exterior lighting, LED-type ambient, emergency and security lights and lighting equipment, ancillary jumper-duplex outlets, mobility and lid opening motors, gearing, gear boxes and related belts, chains and sprockets, and autonomous movement gearing or sprockets, axles and or wheels, knock-out penetrations, scale equipment, and scale-related electronics and equipment that may serve in its intended uses. The lid may operate as a manual or an automated tip-lid or slide-lid for the first cavity through interaction with one or more on-board systems that perform opening, closing, unlocking, and locking functions. The container locker also may include an insulative sleeve on a sidewall, the lockable lid and/or floor areas of the container locker to control temperatures inside of the container locker and/or a prescription pocket that may be locked and accessible through one or more access points to the container locker, wherein the prescription pocket may be interiorly secured within the first cavity and independently accessible from an independent sidewall hatch or locking opening, or separate independent outside areas of the container locker. The container locker also may include at least one interior camera that takes photographs and/or video of the at least one parcel inside the first cavity, wherein the photographs, related data, and/or video are transmitted to at least a sender, a recipient and/or a deliverer of the at least one parcel to confirm that the at least one parcel is verifiably secured in the container locker or has been retrieved from the container locker and at least one exterior camera for security and remote user interface purposes when relocating (driving) the container locker that takes photographs and/or video of exterior areas proximate the container locker wherein the photographs, related data, and/or video are similarly transmitted to at least a sender, a recipient and/or a deliverer of the at least one parcel to confirm that the at least one parcel is verifiably secured in the container locker or has been retrieved from the container locker. The container locker may further include a solar collector preferably positioned on top of the lid, wherein the solar collector may collect solar rays/heat and convert into electricity to charge on-board batteries, operate the container locker, and/or charge devices connected to the container locker. The lid may open to provide an unobstructed opening for manned or unmanned aerial or robotic delivery or retrieval of at the least one parcel from the first cavity. The container locker also may include a retractable or other type of security tether that may connect the container locker to an immovable object to secure the container locker in place and prevent theft, one or more computerized GPS devices, cameras and motion sensors configured to generate one or more shut audio or visual alerts indicating a breach or attempted breach of the container locker, circuitry, antennas and related equipment configured for generating transmission of one or more wireless or cellular signals to provide connectivity to local wireless or cellular communication systems to provide, repeat, and boost signals to and to provide locational information of the container locker, one or more wheels affixed to a bottom portion of the container locker; and wheel covers that protect surfaces as the container locker is rolled or moved across the surfaces, and on-board refrigeration and/or warming devices to maintain internal ambient temperatures to prevent spoilage of contents of the at least one parcel when placed in the first cavity. The container locker also may include at least one on-board ultraviolet germicidal irradiation (UVGI) device or alternative sterilization system to sterilize contents placed into the container locker to sanitize contents, prevent the transmission of contagious diseases, and/or to clean and to prevent the spoilage of contents of the at least one parcel when placed in the container locker.

Other embodiments may provide a TotalVault™ Drone-Port™ ("DronePort") providing a secured, access-controlled area or rooftop or rooftop penetration combined with interior areas of the rooftop housing a plurality of container lockers, the DronePort comprising: a hard surface material forming a base floor area of the DronePort; an access control panel proximate the secured, access-controlled area that is connected to a controller to provide selective restrictive access to the secured, access-controlled area; and at least one security camera to provide security to users of the DronePort, record happenings in the DronePort, and permit users to see at the access control panel who is already present in the DronePort, wherein the plurality of container lockers may be arranged in rows and segments to permit pedestrian maneuvering and manned and unmanned deliveries to each of the plurality of container lockers, wherein each person in a group of people may access an independent container locker of the plurality of container lockers. The DronePort also may include a security fence around a perimeter of the hard surface material forming the base floor area of the DronePort, a security access-controlled entrance controlled through the access control panel, one or more oversized container lockers that may receive larger parcels and/or accommodate when one or more of the plurality of container lockers are not in service, and/or programmable dusk-to-dawn lighting or motion-sensing at or near the at least one security camera to promote safety and usability of the DronePort in dark, darkening, or nighttime periods of time.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which:

FIG. 7 depicts interaction between a container locker according to an embodiment of the present disclosure and an unmanned aerial vehicle or similar device;

FIG. 8 depicts the container locker according to another embodiment of the present disclosure;

FIG. 9 depicts a layout of a scalable facility according to an embodiment of the present disclosure;

DETAILED DESCRIPTION

Figure 1:
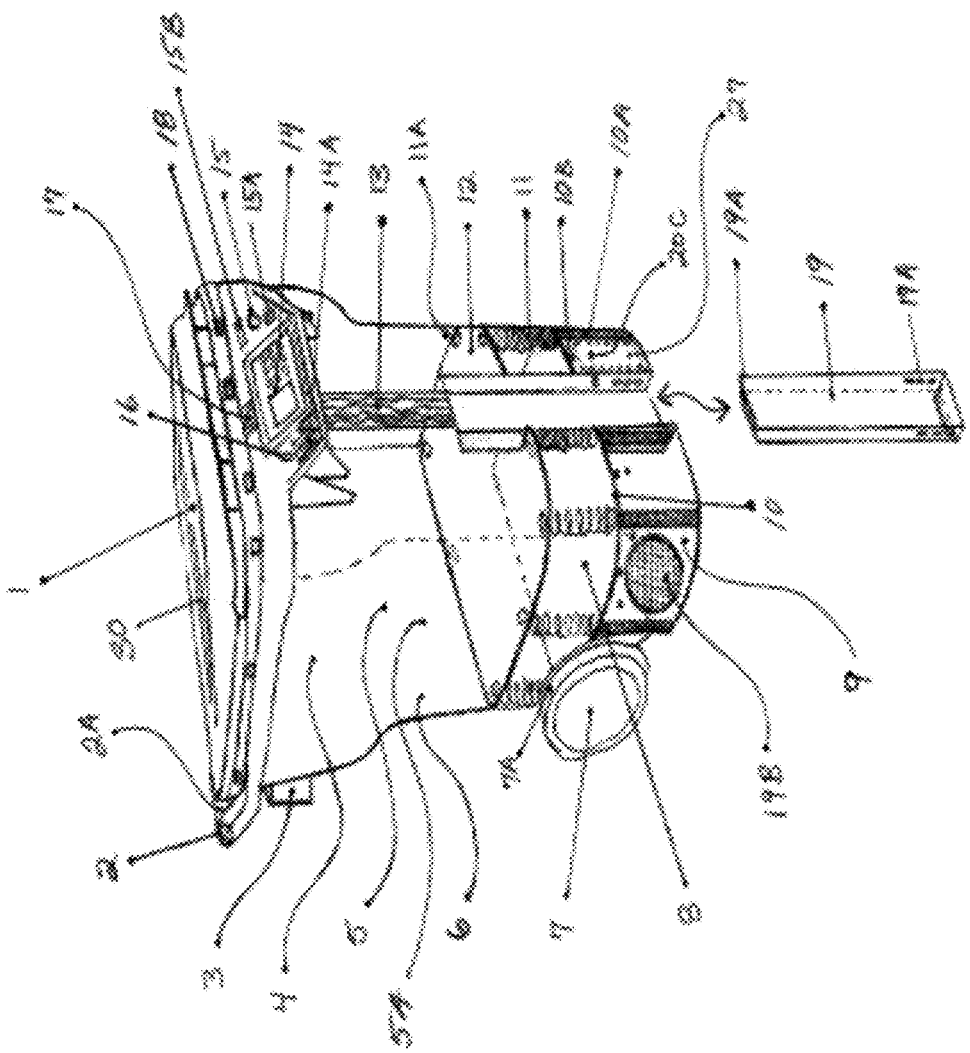
FIG. 1 depicts a container locker according to an embodiment of the present disclosure.

Embodiments of the present disclosure may provide a portable, ground-fastened or permanently affixed, lockable and secured, multi-cavity, weatherproof or weather-resistant, automated, temperature/climate-controlled secured receptacle for manned or unmanned deliveries and pick-ups (referred to as TotalVault™ or container locker herein). The container locker may communicate the date, time, weight of the parcel, and may transmit such data to one or more parties interested in the delivery or pick-up, including, but not limited to, the sender, recipient, and the delivery personnel or entity. Various security features and components may be provided including, but not limited to, cameras 15, microphones 15A, alarms 20B, lighting 4, 20B, motion sensors 15B, GPS and gyroscopes 19, 16, and locational technologies, coupled with one or more on-board computer systems 19 and their operating software, which are typically not reasonably accomplishable securely for the would-be intended recipient if the specified intended recipient of a delivery is not present at the location where and when such delivery is intended to occur. Embodiments of the present disclosure may receive packages, parcels, controlled medicines, documents, and other items of many types and sizes being delivered through delivery means such as delivery personnel, drones and aerial drone drop services and/or other automated and/or mechanic means of the delivery of items.

Embodiments of the present disclosure may provide for the confirmed secured delivery of dry goods and to permit such deliveries to remain in the secured environment of cavity 5 (FIG. 1) until the intended recipient thereof may retrieve them. Depending on the type of item being delivered, after protection of the delivered items from theft, an environmentally-controlled and temperature-controlled environment may be provided for perishable goods delivery and to protect all delivery(ies) from the elements, such as rain, wind, snow, freezing temperatures, overly hot temperatures, and weather in general, after their delivery from a merchant, purveyor or others desiring to make a delivery to customer, specified recipient or other person, especially when such customer, specified recipient, or other person is unavailable to receive the delivery personally and/or has no one to accept such delivery in their stead. In addition to the aforementioned uses, embodiments of the present disclosure may also be used around one's home, office, or, because, in its portable form, it is wheeled, it may fit through a standard sized doorway, is lightweight, and is easily moved around to varied locations for use. Its portability and on-board battery 27 and/or other batteries which may also be placed in other varied locations throughout the container locker, may power various components for a litany of specific purposes, including but not limited to, power delivery capabilities, temporary food refrigeration or warming, warming tasks while cooking out, having a bar-b-que, picnicking and the like, boost Wi-Fi signals from through antennas 16, operate as a wireless, hard-wired or digital tether through on-board electronics 19 to link cellular and other wireless networking and boosting, provide additional electrical outlets at such remote locations or sites, and provide for the secured storage of items in the container locker while situated in and around remote areas of one's home, office, a campsite and the like.

FIG. 1 depicts a container locker according to an embodiment of the present disclosure. As depicted in FIG. 1, a container locker may include three primary cavities or spaces 5, 8, 9 that may be stacked on top of one another and joined together and electronically integrated. Cavity 5 may be referred to as the main cavity or the temperature or environmentally controlled container area. Cavity 5 generally may provide the largest container space with a wide opening at the top that may be covered with one or more automated or non-automated lids/tops. Cavity 5 may be used for receiving and/or holding parcels, packages, boxes, bags, and other items that may be delivered to the container locker. Cavity 5 may be considered the top-most cavity in the container locker and also may house prescription pocket (Rx pocket) 27, which will be described in more detail below.

For highly regulated deliveries such as those with controlled medicines and controlled substances, especially like marijuana and marijuana products, addictive opiates and other drugs, the locker may include an automated drug delivery system which verifies the patient's identity and controls the number of refills issued to the patient according to the prescribed dose and schedule that may, through GPS and other secured and recognized means be delivered to the locker in the patient's absence. The locker may contain separate secured and locked dispensing box or pocket 27 with one or more compartments interiorly secured as a separate locking sub-domain or separately secured space of main container area in cavity 5, such area or pocket (the Rx Pocket™) being inside of the secured area of the main part(s) of the larger container wherein the dispensation (delivery) of pharmacy prescriptions and medicines may be legally and lawfully be placed for the owner/user. Rx Pocket 27 also has utility for the delivery of other highly valuable or confidentially delivered items such as legal documents, jewelry or other small expensive or important items and/or other important confidential and/or delivery-regulated and/or climate control needed items which may be deserved of another layer of security when such delivery may be desired to be delivered to a recipient in his or her absence and where such delivery, once made, is not accessible by children or others that do not have the proper code or means to unlock the area and to provide sovereign access for the user in order to retrieve his or her prescription or item. Electronic communication system 19 and 16 of the locker may be specifically designed to be programmed or otherwise configured to alert and document the delivery personnel, the recipient, the pharmacist, druggist or pharmacy, the prescribing doctor, and others interested in the confirmation of the secured delivery of such prescription that the medicine or items have actually been delivered to an ultra-secured space and that same are, as of delivery confirmation, waiting for the patient to retrieve them via electronic transmittal or data transmission. De-risking this delivery equation for the dispensers of such controlled medicines with the several forms of documentation and confirmation to all parties interested to the delivery of these controlled items is as important to the sender thereof as it is the receiver and the locker may provide every party with the data and information necessary to bring this convenience to the parties in this realm, In some embodiments, when the locker is interconnected with or otherwise interfaced with automated drug or medicine delivery systems or other wirelessly or hard-wire communication oriented connected delivery formats, the automated (manned or unmanned) drug delivery system may require the use one or more verification protocols, PINs, codes or verification forms to verify the prescription details and the patient's registered identity and, as dictated and controlled lawfully by the prescribing doctor and or pharmacist or druggist, may resultantly control the number of refills issued to the patient according to the prescribed dose and schedule. Integration with these dispensers is made wirelessly or through hard-wire connectivity to the locker's computers or systems through to the dispensary's computer servers and/or systems through the internet, via cellular or other electronic means and the locker's on-board communication systems 16 and 19 per the recorded and enforceable agreements previously made between the dispensary, dispenser (pharmacist or druggist) and the recipient/receiver or patient via for deliveries and pickups as prescribed by such agreements.

Some embodiments, due to the regulation and importance to patients to receive their medicines on time and securely, may be provided in a smaller size from the larger versions of the present locker for a senior citizen or other person with a disability or mobility issues. This separately designed and utilized version of the locker would, in a smaller profile, provide a locked dispensing box with one or more compartments and many of the electronic security and features as the larger scoped version but would be used by the owner/user simply as a wirelessly or cellularly connected Rx Drop Box, such as the Rx Pocket in the locker, but separate and independently constructed and used for "only" pharmacy and drugstore related and for, in some cases, Rx-regulated types of deliveries, and the patient/user, pharmacy, pharmacist or druggist, prescribing Doctor and others interested in the confirmation of the secured delivery of such prescription that the medicine or items have actually been delivered to an ultra-secured space and that same are, as of delivery confirmation, waiting for the patient to retrieve them would be similar, if not identical to that which the larger rendition of the locker would provide. These smaller highly secured versions or embodiments of the locker would either be permanently anchored at a convenient location for the parties on the receiver's property or could similarly be made portable and tethered or otherwise anchored to prevent theft and are designed for the receiver to retrieve the entire container to bring it into his or her home to collect the medicines or prescriptions therefrom. This may be designed for senior citizens whose inability to go to the drugstore or other limitations to their mobility to do so are afforded an opportunity to receive their medicines at their doorstep for convenience and their health overall.

Cavity 5 may be covered and/or sealed with lid 1 made of various plastics, metals and or other substrates which are conducive to the construction of same and preventing unauthorized parties unforced access through the orifice opening to the cavities' interior areas and which may, generally, deter them or otherwise dissuade them from gaining entry into the locker. In some embodiments, the locker and its contents, as placed inside, may be secured with locking sliding lid 1 (TOP™ Total Open Porthole Lid™), hereinafter referred to as the "TOP Lid" or lid 1. Lid 1, in several forms and formats, may be designed to slide laterally and tip its cantilevered end downwardly toward the ground or floor as it opens the main portal or opening of the top of cavity 5 of the locker as it opens from one side (front or side) of the container) to the other (the backside or juxtaposed side) as it opens and reverses to close. Some embodiments may use an electric single or double shaft worm gear type motor, or other types of high torque motors and sprocket, belts, and/or chain-type system utilizing one or more motors or sprockets and/or alternative steel lead screw set with mounted ball bearing and shaft coupling type of a motorized corkscrew type or articulating hinged type closing mechanism (like a garage door opening device utilizes) will be employed to perform the opening and closing function(s). In other embodiments, slide lid 1 and lock or locking mechanism 18, like one would see on a roll-out styled waste or trash container (FIG. 8) commonly used as a trash receptacle in residential and commercial settings, may use a single or dual shaft, generally high-torque electric motor and sprocket (or gear) system 3 to open the top of cavity 5 when manned or unmanned means are depositing or retrieving contents from cavity 5. Lid 1 allows the top to flip open 22 approximately 270 degrees from its origin and lie (or hang) down along the vertical side/edge of the locker's backside when opened in order to expose and provide access to open up the entire opening of the top of the locker (FIGS. 2, 8) to make it easier for a UAV or drone or other automated delivery functions, such as delivery robots, to emerge to be used when loading the container or retrieving an item related to an intended delivery or pickup.

The materials comprising the floor of cavity 5 may be rigid, durable and washable and may float above or otherwise be suspended on drop-cushion spring system 11 and/or other cushioning system to protect package contents as a parcel is dropped into cavity 5 from above the locker. The floor of cavity 5 may also serve as a scale deck or platform used in conjunction with the digital load-cell and weighing system below it in cavity 5 or cavity 8 and/or around its surface edges and as connected with the other on-board electronics and computer(s) 19 and/or other exterior networked computers through wireless networking means provided by its on-board systems used in the weighing of contents, the digital or photographic recording of this activity and the wireless or hard-wired transmission of data relative to the delivery and the weight of the contents placed into or retrieved from cavity 5 which may be transmitted to interested parties as deliveries or retrievals are made using cavity 5.

In some embodiments, the bottom (floor) area of cavity 5 may be elevated or suspended above the bottom of the main cavity floor or the interstitial space directly below it, typically cavity 8. While elevating and/or suspending the floor diminishes the useable area of the main cavity of the locker, it generally leaves enough space for the largest of average sized delivery parcels to be placed in cavity 5. Constructing a raised floor results in the creation of an interstitial space between the bottom of the suspended floor of the main compartment (or compartments) underneath in the bottom of the locker to house components, devices, and other things or items that are instrumental in the utility general use of the locker as a whole but which are out of sight and protected. This area is out of sight when peering into the main area(s) of the locker from above with top Lid 1 opened, being hidden below the floor or scale-deck to the observer or typical subject user peering into the locker. Cavities 8, 9 below cavity 5 may house and centrally locate for use throughout the locker a wide variety of electronics 19, wiring, load-cells and weighing instrument 8, speakers 19B, horns 25B, components and parts 8 and 9, such as but not limited to, thermoelectric refrigeration and warming equipment 5, 8 and 9, other refrigeration machinery or equipment 5, 8 and 9, wiring 13, 17 and 20, retractable and/or other electrical plugs, cord and wires 24, retractable and other forms of lock tethers or cords and locking mechanisms 25 and 25C, computers 19 and computer-peripheral devices 8 and 9, and other operationally related devices, appliances and items located in and/or connected to locations throughout the entirety of the locker to comprise a series of integrated systems that work in harmony in the operation and security theft prevention.

Cavity 8 may provide an interstitial space between cavity 5 and cavity 9. Top (ceiling) 12 may be a spider-lifted scale deck or floating or cushion landing surface sitting on or above drop-cushion spring system 11 for dropping packages or parcels into cavity 5. Cavity 8 may be positioned directly below cavity 5, and in some embodiments of the present disclosure, the floor of cavity 5 may be the ceiling of cavity 8, thereby dividing into two cavities. This floor also may provide a cushioned flooring structure designed to cushion parcels landing in cavity 5 from becoming damaged, as they may be suspended using a spring-loaded or other similar cushioning system. The floor also may serve as a scale deck for weighing contents placed into cavity 5, and if so, the floor may be connected to a digital load-cell, flexure system, or spider support and supporting electronics, wiring and sensors causing its operation as a scale that may be housed in the space of cavity 8 in an embodiment of the present disclosure.

Cavity 9 may house mechanical and electrical equipment including, but not limited to, refrigeration or heating/warming thermo-electric or other heating/cooling types of equipment, batteries of various sizes for varied needs, battery-well access hatches and locks, security cords, power cords, gyroscopic devices, motion sensors, speakers, horns, piezo-electric sounders, interior or exterior lighting or LED-type emergency security lighting equipment, ancillary jumper-duplex outlets, mobility motors and related autonomous movement gearing or sprockets, axles and or wheels, and, among other things, knock-out penetrations for future use, scale-related equipment like the scale deck spider, or flexure-base deck support, the scale deck, a digital load-cell, scale equipment, and related and unrelated scale electronics, and other devices, appliances, wiring, components and computers and other items.

Embodiments of the present disclosure may weigh the delivered or retrieved parcels to confirm and verify the correctness (or incorrectness) of the delivery or retrieval made using weigh scale system 8, 19, 12. Once a parcel is dropped and is situated on scale deck 12 in cavity 5, the weigh-scale system of cavity 8 may tabulate the parcel's weight and transmit that data using computers and systems 19 to interested parties. If a parcel is retrieved from the locker, the weight removed from scale deck 12 and load-cell 8 underneath it may be tabulated and transmitted to interested parties as well. Once UAV 31 has dropped its payload or retrieved an item for return, UAV 31 will move away from the drop zone area and hover while continuing to communicate wirelessly with the locker. These communications, will, in addition to the transfer of other data will trigger lid 1 to close, and, once closed, re-locked and complete, UAV 31 may depart its drop zone and return to base or other point of origin. While data transmittals and other communications may be transferred back and forth through wireless, perhaps cellular-type connection between the locker and the UAV or other unmanned mechanical apparatus, parts or all of the data collected in the delivery or retrieval may be compiled and stored and or wirelessly or hard-wire transmitted to a server, the cloud and/or other digital storage means for storage and future use by the parties related to the purchase, sale and delivery or retrieval of parcel 32 delivered or retrieved. Such data might include, but not be limited to, confirmations of data transferred between UAV 31 and the locker through the communication systems of both, descriptions of the contents in parcels 32 delivered or retrieved, operating statistics for UAV 31 and the locker, confirmation(s) that lid 1 was closed after completion of the delivery or retrieval, confirmation that maglock system 18 was re-secured and locked down, photographs taken in the locker or around the locker of the newly placed or absence of the then retrieved parcels or contents or delivery personnel performing their retrieval or delivery duties by camera 15 or other cameras 28, photos or video of the delivery or retrieval event itself while being undertaken by cameras 15 and/or 18, videos or photos and weights associated contents placed in or retrieved from re-locked cavity 5 of the locker and a multitude of other reasonably useable conformational data regarding the delivery or retrieval.

Lid or cover 1 may utilize a mechanical, magnetic or other form of locking mechanisms 18 to ensure that deliveries, once received in the container are not accessible to others outside of the intended recipient or those with proper codes, PIN numbers or other approved means to have access thereto. Locking mechanism(s) 18 used may be integrated with the device's on-board computer and other computers, electronic components and systems and software controlling the use of the apparatus. These locking mechanisms may be integrated with and communicate with the device's electronics and/or communications systems using those components and their software present in the device and other devices interacting with it. In some embodiments, a simpler electronic or mechanical lock system may be used in lieu of the aforementioned maglock style locking system.

Various forms of electromagnetic, electromechanical and mechanical forms of locking mechanisms 18, including regular physical lock and key types of locks, and the inclusion of other electronics, electronic wiring or mechanical components, like handle 2A to activate such locks and which may be used in and comprise a part of the construction of the locker may be configured to lock out would-be thieves and others from gaining access to interior areas of the container where packages, parcels, bags, pharmacy products and other items are temporarily stored for the user/recipient in cavity 5 or Rx Pocket 27 until the intended recipient can retrieve them. In some embodiments, the lid locks for lid 1 and Rx Pocket 27, protective caps or covers, and/or other sub-domain areas if any, may use padlocks, combination locks, compact sized cam locks or other locks like those used in containers, cabinets, drawers, drug cabinets, credenzas, sliding doors, lockers, mail boxes and other door type applications where such compact size can permit for the lock to fit in an existing cam lock sized opening and provides electronic access via a keypad and display 14 or other electronic access depicted in 27, such electronics being operated by hard-wired, AC, DC or battery backup power sources. In other embodiments and depending on design, using batteries, such as AAA or D size batteries or smaller or using keys or codes, PINS or may also be used to lock or unlock portions or cavities, to turn a knob or a handle, or to otherwise utilize electronics that release a lock turn knob or handle when the correct access code or biometric data is entered may be utilized.

In other embodiments, varied types of locks, especially electromagnetic locks 18 and their wiring 17, keypad and display and communications center (comm center) 14 and 27, wherein an electromagnetic lock, magnetic lock, or maglock as a locking device may include one or more electromagnets and an armature plate(s) in varied forms, are employed to deny or permit access to interior secured areas of the container locker, such access being granted through electronic access via keypad and display 14 through the use of a PIN Number or other electronic coded access key through keypad and display 14 as a part of communications center 14 or 27 to the locker or other sub-domains thereof. Such electromagnetic locks may be configured as be either "fail safe" or "fail secure" wherein a fail-secure locking device remains locked when power is lost and a fail-safe locking device is unlocked when de-energized from power provided from on-board batteries 27 or through other sources using the power cord and plug 24 or low-voltage connector 26. And yet other embodiments may utilize other common lock and key technology and/or other system-integrated electronic and/or mechanical or hybrid forms of locking and locking mechanisms in places throughout the locker to secure and prevent unauthorized access to one or more areas of the cavities or areas. A simple lock and key may also be used to secure lid 1 to the base of the container locker.

Cavity 9 may be positioned below cavity 8, and its base/bottom may form the bottom of the container locker as depicted in FIG. 1. Floor 10 is the ceiling of cavity 9 and the floor of cavity 8. It may be made of a variety of substances including but not limited to plastics, fiberglass, metals or steels and/or others, being suspended and supported by an engineered riser to create space in between the floor of the container and the bottom of cavity 8. Floor support legs 10A may support floor 10 and may be molded, screwed, or riveted support posts or attachments provided around the edges of floor 10 where or near where it meets the sidewalls of the cavity. Floor support posts 10B may be molded, screwed, or riveted support posts or attachments provided around the edges of floor 10 to secure the surface of floor 10 to the sidewalls of the interior of the container locker to support the load of equipment in cavity 8.

There may be a soft-landing floor that also serves as scale deck 10 (FIG. 5) on the interior of cavity 5. Floor 10 may be constructed of a wide variety of materials including but not limited to plastics, fiberglass, metals, mesh and other substantive substrates and/or materials which are conducive to the wear and tear that the floor of the locker will endure. In some embodiments, the bottom of the installed floor of cavity 5 sits upon a series of springs 11 (FIG. 6) fixed to the floor or sidewalls of the raw container and which is connect also to the bottom of the suspended floor 10 below it, mounted to the sidewalls and the bottom of cavity 9 below it to provide stability to the construction of the locker. One familiar with the art will recognize that other alternative designs to segregate areas or cavities as otherwise conceived which may also provide for more efficient means of the stacking or arranging of cavities or, perhaps the deletion of one or more cavities may lend themselves to added utility and/or the decrease in cost of the manufacture or use of the locker. Alternative designs to weighing contents, such as the use of aluminum, metal or other forms of netting, and those which permit for the suspension of the floor to provide a softer eased landing when drone-dropped and other mechanically delivered items are dropped into the container to provide a cushioned landing and to prevent or deter the breakage or other damage to/of the items being dropped into the locker which are enclosed in the parcels, packages, or bags, etc. when released and delivered as they land in the container may be considered.

Figure 5:
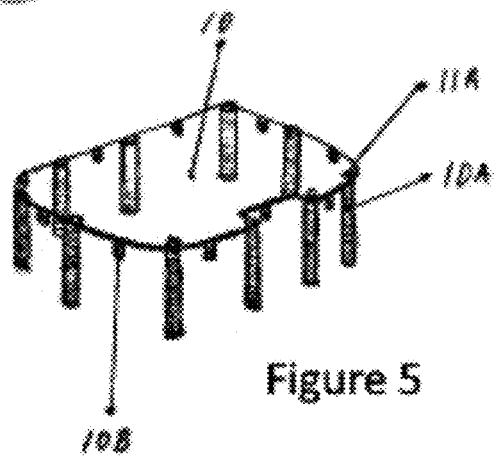
FIG. 5 depicts a view of the sub-floor of cavity 9 of the container locker of FIG. 1 according to an embodiment of the present disclosure.

The floor of cavity 8 may be the ceiling of cavity 9 and may divide the two cavities. Cavity 9 may be formed through a fabricated insert (FIG. 5). Cavity 9 may house the electrical and/or mechanical devices, appliances, and/or systems that may support the operation of the container locker. These devices, appliances, and/or systems may include, but are not limited to, batteries, warming and/or refrigeration equipment, thermoelectric devices and systems, retractable power cords 24 and plugs, retractable security tether cables 25, other solid-mounted security tethers or locking mechanisms, duplex electrical jumper outlets 23, Bluetooth connectible speakers 19B, piezoelectric sounders, audible alarms and/or horns 25B, all of which may be permanently or removably housed within cavity 9. If the container locker is permanently affixed to a location, such as in a DronePort Terminal array, one or more bolts or other fasteners may protrude through the exterior bottom of cavity 9 with washers and nuts tightened to securely attach the container locker. These fastener assemblies may be completely enclosed on the inside of cavity 9 so they are inaccessible to the user but are accessible to technicians and repair personnel by removing the scale deck and equipment and floors above cavity 9 when they may choose to remove the container locker from its permanent location for service or replacement. While three cavities are depicted herein, it should be appreciated that there may be embodiments of the present disclosure where more or fewer cavities may be provided.

FIG. 1 also depicts handle 2A which may be used for manipulating movement of the container locker by hand and/or handle 2A may be used to tether the container locker to immovable objects in the absence of other securing components. Open and closure drive train 2 may include sprockets, gears, chains, and/or motor parts or other hatch-opening components used in the opening and closing of cavity 5 for deliveries or retrievals. Electrical motors 3 may be positioned below open and closure drive train 2 and may also include related gear-boxes, sprockets and/or lid 1 auto-opening equipment or the container locker's self-driving or programmed mobility gearing, sprockets, axles connected to wheels 7 for driving for relocation of the container locker in embodiments of the present disclosure. Wheels 7 may be typically 7.5" to 12" in diameter and constructed of plastics or rubberized materials to protect interior flooring of areas indoors when wheeled thereinto to unload and or operate.

In some embodiments, the container locker may be fitted with one or more wheels 7 and axle(s) 21 with wheel-covers 7A. In some embodiments, the handle system may be a built-in molded handle system to tilt and move (roll) it around easily and, resultantly, makes this locker portable and readily moveable to any user-convenient location preferred by the user for the receiving of packages, parcels and/or items and a multitude of other uses in locations where it may be secured via locking tether 25, plated screw-eye (security eyelet) 25C mounted to the bottom areas of the exterior of cavity 9 and/or other locking or lock-down means such as a docking station (not pictured) securing the locker to a permanent location and/or affixing it to the structure of a building, to insure that the locker and its contents may not easily be stolen from its then current location. In some embodiments, surfaces of wheel 7 may be softened and may be constructed of soft rubberized or other materials of varied sorts or which may be covered with temporary or permanent wheel covers 7A, that may lessen damage to surfaces that the device is moved over and to prevent floors made of tiles, marbles, smooth surfaced stones, laminates and wood, and the like, from being scratched as the loaded container is rolled over them when relocating the container locker. This is especially important to the user/owner when wheeling the heavier-when-full device into one's home or office to unload the device inside his/her home or office setting. In other embodiments, such as when multiple lockers are communally housed in a secured area, like a DronePort Terminal™ facility, the wheels may be removed, and each locker may be permanently fastened to its location with bolts and nuts.

In some embodiments, an additional security benefit may be provided by the container locker being relocated to a safer or more secure location on its own. Using three or more wheels 7 and 7A and proximity or motion sensors and/or cameras, the locker can, using a built-in electric motor 3 to be remotely pilotable by the user and/or may also drive itself, in the absence of a person there at the location to do so, to another location from where it was situated when a delivery or retrieval was made into or out of cavity 5 by using on-board computer 19 connectivity with electric motor 3 or additional electric motor 3 housed near wheels 7. In this case, the locker being wirelessly linked using its on-board comm-center systems 19 and other on-board devices and appliances contained therein, like antennas 16 and cameras 15, in conjunction with other off-board systems and computers, most likely also using cellular technologies, and software and GPS technologies through a software application (i.e. an App) on the user's remote cell phone, computer, or smartpad to trigger the maneuver, the entire locker can engage the motor and gear box connected to wheels 7 and can drive itself to a predetermined location prescribed in advance by the user that is safer until he/she can gather the contents at a later time. The locker according to embodiments of the present disclosure can also be programmed to accomplish this automatically at predetermined times based on predetermined variables such as, after the locker is opened and a delivery is made, drive to X-spot in the garage interconnectivity with a garage door opener model on-board, the locker could allow it to open the garage door, drive into a predetermined spot in the garage and to close the garage door behind it. One familiar with the art would also recognize that interconnected wirelessly operated or automated off-board systems like a garage door, an electronically locked and digitally operated gate or the like might also be interconnected to allow same to open to provide the locker with a clear path and/or access to such secure areas such as a garage or behind a gate, or, even, to a predetermined location along or behind a structure or fence which might be hidden from sight to passers-by and or would-be thieves seeking to force access into the locker's cavities and steal the goods in the user/owner's absence. Interconnectivity with other security and access type systems provides limitless utility whether the user is on an app driving the locker, or the locker may be pre-programmed to maneuver to another location after a particular event has triggered it.

The container locker also may include interior automatic lighting 4 that may automatically light the interior of cavity 5 and/or prescription pocket 27 when the container locker is opened for use. Exterior 6 of the container locker may be reflective and/or glow-in-the-dark and may be comprised of plastics to provide high visibility in dark or darkening environments. Plastics may provide highly luminous reflective exterior surface 6 when exposed to direct lighting in dark or darkening settings (like that that headlights of a car truck or van on a highway sign provides) and, even, the ability for the same surface 6 to glow in the dark when it is situated in darkness after being exposed to light to absorb sunlight throughout the daytime to charge the apparatuses' exterior surface's 6 to sunlight and chemically generate its glow at night.

Communication center keypad and screen display 14 may include, but is not limited to, a microphone, motion or other sensors, cameras, cellular telephones, USB or other connectivity ports, a visual display or screen with optical (eye), facial, fingerprint or other biometric identification reader (sometimes in conjunction with camera 15), and a keypad bearing digits, symbols or alphabetical letters or other numeric, alphabetical, thumb or fingerprint for biometric identification used for human or other interaction with unlocking the container locker, communicating through its systems or other manipulation of the systems used in the container locker, including, but not limited to programming its systems, or controlling its security or other functions as interfaced and interconnected with its computers and systems. USB connectivity port 14A may provide one or more USB interface ports for connection to the systems, computers, devices speakers, security systems, appliances and/or all connectible systems on-board or remotely in the container locker. Camera 15 according to an embodiment of the present disclosure may be a 1080p camera including night-vision capability with a fish-eye camera lens used in bar code scanning, security, communications and other operations with and through the container locker as connected to systems contained on-board and/or networked to or through remotely. One or more microphones 15A may be used in security, communications, and other operations with and through the container locker as connected to systems contained on-board and/or networked to or through it remotely. One or more motion sensors 15B may be used for security, communications and other operations with and through the container locker as connected to systems contained on-board and/or networked to or through it remotely.

The locker may be interiorly or exteriorly insulated in a variety of ways, including, but not limited to, using insulative properties in the materials used in the construction of the side walls of the locker, the use of an interior or exterior insulated or fitted sleeve or interior or exterior jacket 5A around the some or all of the locker, use of blown-on materials inside or outside of the container and/or the container walls 5A may be constructed using insulative materials to provide related cooling and/or warming properties and/or to create a barrier 5A between the received contents of the locker and areas outside of the container by filling an insulative interstitial space in between layers of the side-wall materials (inside and outside of the locker to create an area buffering the inside of the locker container, including areas on the underside of lid 1 from the elements outside thereof and creating an interior contents delivery space that can be more easily climate controlled with the refrigeration and or warming devices 9. Insulation sleeve 5A may provide an insulative component or insulation built into the container sidewalls. Other removable or non-removable, interiorly or exteriorly applied insulative jacket, sleeve or other adhered materials may be provided to control temperatures inside of cavity 9 and/or prescription pocket 27 or other cavities. Wiring harnesses 13 may be used to electrically connect appliances, batteries, devices, computers, lighting, or other equipment throughout the container locker.

Cavity 5 of the locker may be injection-molded, rotomolded or may use other forms of construction related to the manufacture of containers, lockers, coolers or iceboxes and the like including, but not limited to welding, stamping, printing and other alternative forms of constructing a container. One embodiment may use a construction much like that of an ice-chest or cooler wherein the walls of the locker container may be molded and filled with materials that have insulating properties that either increase or decrease cooling or heating loss or heat gain inside the locker relative to the exterior of the locker. Another embodiment may insulate parts of the interior receiving area(s) of the locker with various types of materials 5A that inhibit heat transfer between the inside and outside of the locker that may snap or adhere/attach onto the interior walls of the container or onto the outside of the exterior of the locker, may be magnetically bound or otherwise adhered permanently or temporarily to the interior or exterior or otherwise may be attached to the container by the user to insulate contents as desired. Some of these materials may be constructed as inserts which may be permanently or temporarily installed in the interior as the user/owner prefers for use of the device and depending on what specific types of contents are being anticipated for delivery by the owner/user. Insulated inserts may also, in some embodiments, be used as a jacket, bag or type of warming or cooling bag container that delivery personnel or drones actually transport the items, like, but not limited to, groceries, in to insulate, warm or cool and otherwise preserve the items while in transit when they are being delivered from their origin to the recipient. Once at the location of the locker, the entirety of the insulated bag, including the items delivered in it, are placed into the locker insulated cavity to further maintain temperatures and preservation until the recipient retrieves the delivery from the locker.

Drop-cushion spring system 11 may use springs, spring-loaded sleeves, elastics, cushioning fabrics or other means to cushion the blow of packages or parcels being dropped into cavity 5. Floor insert supports 11A may be molded, screwed, or riveted support posts for fastening or otherwise connecting the floating/drop-cushion floor and scale deck 12 to supportive cushioning spring system 11. Floor and scale deck 12 may use cushioning system 11 to lighten the shock of dropped packages in cavity 5 and may provide a scale deck used with a load-cell and scale system to weigh or tabulate items that may be placed into or retrieved from the floor of cavity 5. Embodiments may utilize a digital load-cell, and or a hydraulic transducer, often referred to as load cell 8. A voltage may be applied to the device and/or its sub-system, and the weight causes the current through it to change. The current may be converted to a digital number by an analog-to-digital converter, translated by digital logic to the correct units, and displayed on the display to indicate to the user or system reading same the weight of the object as measured in the aforementioned units. Usually, the device and its system or sub-system will be run by on-board computer 19 and its embedded microprocessor chip that tabulate, tally and forward on to interested parties, the data and other information tabulated, dated, tallied, etc. that is associated with a particular delivery and/or pickup as the item(s) is/are placed into or retrieved from cavity 5.

The locker may operate its electronics and systems 19, 14, 15, 16, 8 and others internally using low-voltage circuitry, preferably in the 12 v DC range and may be connected to other DC power sources to charge or operate and or may be connected to alternating current (AC) sources of electricity through its electrical cord and plug 24 to either operate or charge on-board batteries 27 via the use of varied AC to DC and/or DC to AC adapters located in cavity 9. Some versions of the locker may just plug in and may operate on normal common (US) 120 v AC (60 Hz) mains electricity. The printed board circuitry (PCB) 19 may be engineered for a 12-volt standard for construction and operation with the capability to be connected to other mains power source voltages using commonly adopted AC-to-DC transformers. In the United States, where hard wire connected, the device may be plugged in and powered with normal common 120 v AC (60 Hz) mains electricity from a typical electrical outlet used widely throughout the US through the electrical cord and plug 24 and jurisdictions thusly powered therein. Other embodiments which are designed for areas outside of the U.S. may utilize different electrical designs and voltages that are commonly or customarily utilized indigenously in the areas where the locker is used, deployed, sold or provided understanding that electrical cords and plugs 24 would necessarily be modified for these areas and locations. Alternative embodiments contemplated will utilize rechargeable low-voltage on-board DC batteries 27 to operate the apparatus or some parts of it and its related systems. Where such batteries 27 are employed in the use of the apparatus, connectivity to common house current through a standard electrical outlet may also provide for the operation of the device in lieu of the batteries when plugged in and such connectivity may also trickle-charge the on-board batteries 27 simultaneously. When unplugged from a house mains electrical source, the locker may be energized through on-board batteries 27 in its entirety. Many embodiments may utilize a low-voltage on-board electrical system for electronic and or digital, lighting 4, 20B, 20C, cameras 15 and 28, alarms 19, 19B, and 25B and the operation of a cell phone and/or computer 19 and the like used in the operation of the device and which are that are intended to be operating as a part of the locker's use. Other embodiments may also have a port or ports to plug in and charge or operate other devices through the locker's connectivity or batteries when plugged into the device for charging or use to boost or extend wireless connectivity radii 16 and 19 to be used by the appliance itself and/or other nearby wirelessly connected devices as well. Although other voltages and configurations might be utilized, common voltage ranges for operations and use of the appliance would typically fall below 49 volts (as defined by the United States 2005 National Electrical Code (NEC) defines low (distribution system) voltage as 0 to 49 volts), and more specifically, likely between 3.0 volts DC and 30 volts DC. In foreign jurisdictions, and, in AC-designed or configured systems, "low voltage" may be defined by The International Electrotechnical Commission (IEC) definition for low voltage, typically meaning, "Between 50 v AC and 1000 v AC.

Some embodiments also may include a docking station form of locking system which secures the locker in one location and which restricts the apparatus from being easily removed from its intended location. This system of locking down the locker may use docking station connector 25C, which may use plated screw-eye (security eyelet) 25C and using interior and exterior substrate plates for reinforcement and which is mounted to the bottom areas of the exterior of cavity 9 and permanently affixed to the bottom sidewall of the locker may include a variety of means and of the utilization of a preferably metal pre-designed wheel-over locking mechanism that the locker may be easily wheeled or drive itself over to rest in place securely and be released from the locked position using a foot activated pressure plate (not pictured herein), once the proper security code has been entered and recognized by the onboard system(s) and computers and software 19. Locking wheels may also be used in addition to or as an alternative to a docking station and/or other form of security tether to prohibit the locker from being easily moved, relocated and/or stolen from its intended location.

Antennas 16 may broadcast and/or receive signals used in the operation of the container locker including, but not limited to, use in cellular, wireless, Bluetooth, drone-drop or unmanned vehicle transponder protocols, Internet of Things (IoT) protocols, and/or other signals and connectivity as connected to systems contained on-board and/or networked to or through it remotely.

The locker may be outfitted and configured to be used to provide wireless signal strengthening as a WIFI booster through a booster device or as a repeater or connection and/or relay point in an array of 4G, 5G or other similar protocol relay points embedded in electronics housing 19 or elsewhere placed using antenna 16 and, further, through its on-board electrical communication and power components 19 and wireless connectivity in, to and through electronics housing or sleeve 19 through connectivity to antenna 16's capabilities providing a relayed WIFI boost to strengthen the signal strength and connectivity between the device and remote wireless signal generators (such as modem-routers and other types of routers in nearby areas serving the setting) and to strengthen signals to other nearby wireless devices which may be connected to and through the wireless signal(s) that the appliance is wirelessly connected to as a convenience to its user and to more fully complete an array of connection points as are used in 5G.

Wiring harnesses 17 may be used in electrically connecting appliances, batteries, devices, computers, lighting and other equipment throughout the entirety of the container locker. Locking system 18 may be electronic, mechanical, and/or magnetic and may be used in securing the contents of the container locker to prevent unauthorized access to items in the cavities. It may be interconnected with other systems contained on-board and/or networked to or through it remotely.

Speakers 19B may be exterior speakers installed in the outer walls or adhered thereto. These speakers may be integrated with on-board systems to be used in communication, security and convenience functions and operations to provide audible voice, tones, music and other broadcasted sounds for a variety of functions and operations for security purposes and or the user's enjoyment. Wiring harnesses 20 may be used in electrically connecting appliances, batteries, devices, computers, lighting and other equipment throughout the entirety of the container locker. Battery-well hatch 20A may provide a locking hatch and a point of access to on-board batteries.

LED exterior lighting 20B may be located at or near the top of the container locker for use in security alerting and/or providing ambient lighting proximate the container locker. Exterior LED alarm flashers 20C may be provided around the base of the container locker approximately 1' above ground level wrapping the container locker's base with exteriorly visible emergency lighting flasher lights, typically red in color, that may blink or flash when the container locker is in an alarmed status. This may be used to create ambient light or to flash to indicate to the user and others that the container locker has been breached and/or is otherwise compromised or at risk relative to programmed security measures.

Figure 2:
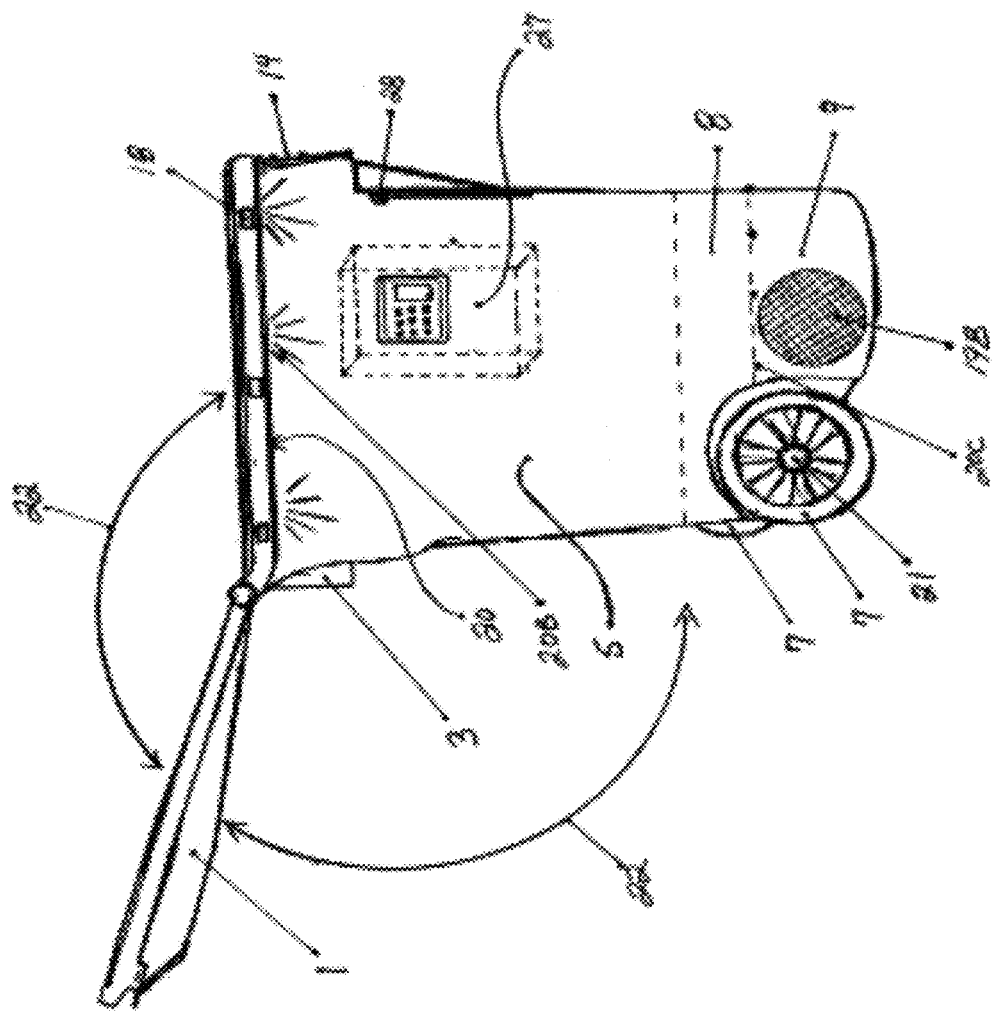
FIG. 2 depicts a side perspective view of a container locker according to an embodiment of the present disclosure.

FIG. 2 depicts a side perspective view of a container locker according to an embodiment of the present disclosure. As depicted herein, lid/top 1 may be opened or retracted to clear (open-up) the entirety for the use of manned or unmanned access to the container locker, particularly cavity 5. Lid/top 1 may be constructed of a hard plastic or other impenetrable material. It may either be physically opened by a person or it may operate as an automated tip-lid or slide-lid main orifice hatch-cover for cavity 5 that is interactive with and interconnected with on-board systems, devices and appliances to perform opening, closing, unlocking, and locking functions for manned and unmanned deliveries or retrievals using computers and on-board motors, gears, sprockets and the like to open, close and lock.

Other parts of the container locker also may be accessed in this manner including, but not limited to, prescription pocket 27. Prescription pocket 27 may be accessed through an independent locking hatch in some embodiments of the present disclosure, but it also may be accessed through cavity 5, though with independent locking, security, and/or access points, doors, hatches, or other means. There may be other embodiments of the present disclosure where prescription pocket 27 may remain separate from other areas/cavities of the container locker to provide additional security for those medicines, drugs, or other sensitive deliveries or pickups to be made, such as legal documents, jewelry, or other small expensive, important, confidential, delivery-regulated, and/or climate-controlled items. In such embodiments, prescription pocket 27 may include separate locking and unlocking systems and means of digital, electronic and/or mechanical keyed or coded access independent of those used to provide access to cavity 5, but which may use on-board equipment and systems, including, but not limited to the computers, systems and other digital security means to remain independently accessed as a separate secured location or space for controlled or regulated deliveries.

One or more axles 21 may be fixed in location and used to mount rotating wheels and/or gears and secure the wheels or gears to specific locations relative to other wheels or gears. In an autonomous mobility function, axles 21 may be used in driving or relocating the container locker and can be connected through gears, sprockets or chains, to on-board electrical motor 3. Opening 22 may provide a 270° opening for lid 1 to permit a wide clear opening of lid 1 to remove it from obstructing the loading orifice when placing items into cavity 5 and/or removing items therefrom, being particularly important in deliveries or retrievals using unmanned aerial vehicles or other robotic machinery. Battery well 27 may provide a compartment to hold and secure a variety of on-board batteries. In an embodiment of the present disclosure, 12 v DC batteries may be housed in well 27 and may be readily accessible through the battery-well hatch 20A, which can be locked and unlocked with a key or other means.

The container locker may employ one or more cameras 15, 28 that may be appropriately placed or located inside of or outside of the locker for the successful operation of it. One or more interior cameras 28 may be provided, typically 1080p with night-vision and flash modes, which may be coupled with or otherwise connected to lighting or flashing mechanisms, to take photographs and/or video of the delivered parcel or contents inside of the container locker. Once a parcel has been delivered, and the container has been re-closed, camera 28 can photograph or video the contents of cavity 5, and networked or on-board communication systems and computers can forward photos or video and a litany of other data regarding the delivery or pickup to parties interested in the confirmation of such delivery via text, email and other transmission means, allowing for photo-confirmation to interested parties involved in the delivery or retrieval that that the parcel was actually handled, was verifiably secured in the container or was retrieved successfully. The cameras may be integrated with the onboard and wirelessly or hard-wire connected system(s), motion, tilt and other sensors 9 and 19, and other external systems to provide a visual photographic or video aspects of security for viewing externally and internally and which may be employed for, among several other things, use in integrated or on-board security system(s), visually confirming (photographing or videotaping) the person or persons, UAV 31 or other manned or unmanned vehicles, the viewing of areas surrounding and/or inside of cavities 5, 8 and/or 9 and prescription pocket 27A, while they are accessing or after they have accessed the them, as the task of entering it is physically performed, and for visually confirming the delivery (or pickup) of items placed in the locker by photographing or videotaping or otherwise recording the presence or absence of an item or items the delivery task or pickup task has been performed and "after" the locker has been opened, closed and re-locked. These visual confirmations may be stored, transmitted and/or otherwise communicated ones email or cellular phone text and the like through the connected system(s) used in the operation of the locker to parties interested in the delivery or pickup before, during and after the task occurs and can provide a multitude of recordation, security and other utility to the users thereof. The photographs and/or video may provide a time/date stamped evidence that a delivery or pickup task has been performed. Cameras and/or lenses 28 may capture digital video and/or photographic pictures of specific interior or exterior areas of the locker. Such cameras 28, lenses or photographic equipment accoutrements may be installed in the sidewall, lid or bottom (in or under the suspended floor or in the electronics well(s) below same) and facing inwardly or outwardly to provide the users of the locker with the ability to see what is contained in the locker without having to open it physically to do so and would also be able to provide photo or video shots of people delivering and operating the locker using motion sensors 19, and or other means and what is (or was) occurring or happening outside of the locker at a specific time and on a specific date relative to where the locker is situated. When photographing or videotaping interior areas of cavities 5, 8 or 9, camera 28 and its integrated computers and/or electronic drivers may photograph or video the inside area(s) of the cavity(ies) of the locker and communicate or otherwise transmit the photographic data through its integrated systems wirelessly or through hard-wired means to the owner or other parties engaged in the delivery or pickup to provide visual evidence of the task as performed and the confirmation of the completion of the delivery or pickup once performed and the locker is re-sealed and secured.

Photographing or videotaping the inside of the locker with internal cameras 28 may be a means through which a deliverer of goods to the locker can verify that the good was actually deposited into the locker, that the locker was properly closed and locked, and that the contents are awaiting retrieval from the intended recipient of same. This feature can digitally communicate to all interested parties a photographic verifiability to the item's seller, the delivery personnel and the intended recipient alike. The feature may provide visual confirmation that the delivery process has been, in fact, verifiably completed.

In yet other embodiments, one or more cameras 15 and 28, lenses or other installed video equipment and which may be coupled with lighting or flashing stroboscopic-type lighting conducive to photographing or video recording in a dark interior or exterior spaces, may provide, transmit and/or otherwise communicate digital video and photograph information related to areas outside or external to the interior of the locker and proximate various distances from its then current location where situated for security and a variety of other purposes. To those familiar with the art and similar to technologies used in their doorbells, and areas around their homes or offices, fish-eye and other forms of lenses, cameras and photography in general have advanced and continue to develop, all of which may be included in the system on-board the locker and which may be deployed or employed to, resultantly, provide additional utility to the users when networked with other systems and or as a stand-alone servant in those endeavors. In such case where the system(s) are integrated with local or, even off-site security systems, onboard cameras 15, 28 and other photographic and video-taking and recording capabilities through its on-board or networked computers 19, may also be used as configured with such other system(s) to serve in delivering marginal, modular and portable aspects to the general visual security of a place, space or area proximate the device and its cameras and may extend the efficacy of nearby security systems proximate the locker's systems and devices as they are connected a wirelessly or hardwired to record and transmit data and also lend a verifiable computer-aided additional means of date-stamp memorializing (or otherwise providing) video or photograph evidence of activities occurring in and/or around such places, spaces or areas proximate the apparatus' current location as an interconnected video sub-component thereof.

Figure 3:
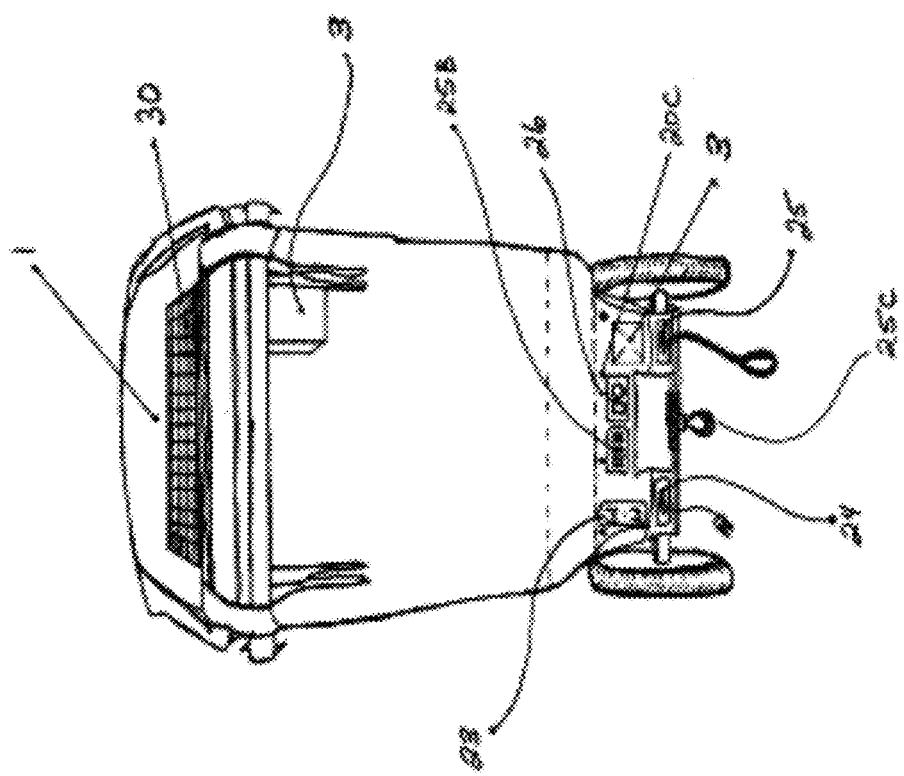
FIG. 3 depicts a rear view of a container locker according to an embodiment of the present disclosure.

FIG. 3 depicts a rear view of a container locker according to an embodiment of the present disclosure. As depicted herein, there may be devices and/or components that may be used in or for (i) collecting solar energy through solar collector 30 mounted facing upwardly on the top of top lid 1 to operate or charge on-board batteries, (ii) operating and housing the gears, sprocketing or chains used operation of opening and closing and securing cavity 5, (iii) the provision of retractable wiring and connecting to exterior electricity sources or other sources therethrough 23, 24, (iv) retractable tether 25 for securing of the apparatus to an immovable object for security purposes, (v) flashing lighting 20C to provide visual signalization to people and authorities that the container locker security has been breached, moved from its intended location, or is otherwise is otherwise unsecured, (vi) providing access points or connections to other features, power sources or useful systems, (vii) audible horns, buzzers or piezo styled security system warning alarms 25B, and/or (viii) tethering or mounting hooks to permanently anchor or dock the container locker in a permanent or semi-permanent location.

Solar energy collector 30 may be situated on top of lid 1 where its efficacy can be enhanced in the sunlight. Solar thermal collector 30 may collect heat by absorbing sunlight and convert this energy into electricity through on-board systems to charge on-board batteries, operate the container locker and/or to charge other connected devices. Solar collector 30 may energize, operate the apparatus and/or to trickle-charge on-board battery 19, batteries 27, or to gather and store or supply power to parts of the entirety of the locker in the absence of 120 v 60 Hz house current or other main house voltage (as configured) or on-board battery 27 power availability and the power system may be designed to use the solar collectors to charge, or otherwise trickle charge, other devices connected to the device itself. In some events and certain configurations where access to a regular electricity source is absent or desired not to be used at all, solar collector 30 may be the sole source of power used to operate different parts of the operative functions of the locker.

Ancillary duplex outlet plug or jumper plug 23 may be provided as a local source of electrical or solar power as a convenience to the user if the container locker is connected to 60 Hz 120 v AC house current. Plug 23 also may connect through on-board batteries 27 to other devices and may be used as an electrical source to provide electrical current to other appliances or tools as a jumper through its connectivity to mains power through power cord(s) 24, to provide the relay of power to and through its onboard duplex outlets or plugs 23 on its exterior surfaces. Retractable power cord or cord reel 24 may connect the container locker to house power to connect it to a power source, typically 60 Hz 120 v AC house current. This power cord, in some embodiments may be self-retractable, like that used in many home appliances. Regardless whether the cord is retractable or not, it may provide between 8' and 15' of cord for the convenience of the user. Retractable security tether 25 may connect the container locker to an immovable object, such as a post, a house, or other anchored item, to secure it in place and prevent theft of the container locker. This security tether 25 in some embodiments may be self-retractable, but regardless whether the cord is retractable or not, it may provide between 8' and 15' of cord for the convenience of the user. Knock-out panel 26 may be provided in the container locker. It may provide a perforated or other similar area such that it may be readily removed, such as by punching, hammering, or cutting, to provide an opening into the interior to be used for access or use of other devices or appliances which might increase utility to the user.

Figure 4:
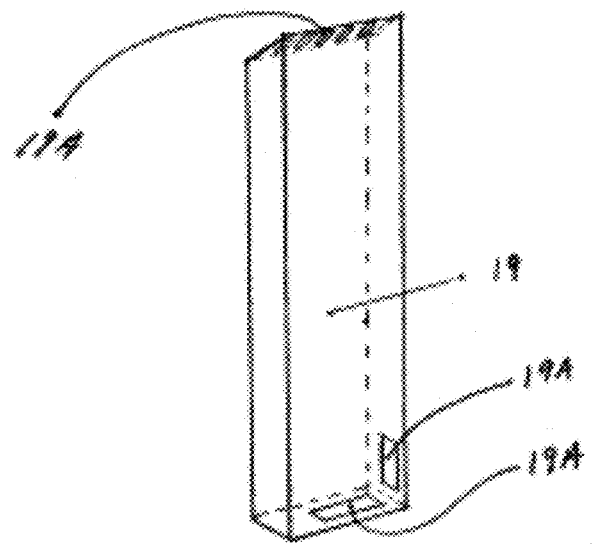
FIG. 4 depicts an indentation on cavity 5 of the container locker of FIG. 1 according to an embodiment of the present disclosure.

FIG. 4 depicts an indentation on cavity 5 of the container locker of FIG. 1 according to an embodiment of the present disclosure. This indentation may be fitted with one or more handles to lift the entire container. In some embodiments of the present disclosure, this area may be modified to provide a mechanism to mount, store, or otherwise utilize other systems or components. This area also may be covered with a plate that may enclose the area and may create an interstitial area wherein many of the sensitive electronics, computers and the like may be housed where they are well-protected from environmental elements such as rain and wind. The electronic components housed herein may be enclosed in a modular retractable secured and durable enclosure made to slide into and/or out of the space or which may be constructed with a liftable cover flap (flap 14, FIGS. 1 and 2) to allow for the installation, removal and/or replacement of the computer and electronics package to modularly be addressed in manufacturing and in repairs needed in the field. While FIG. 4 (as well as FIGS. 19 and 19B) depict a shape of the indentation, it should be appreciated that other shapes and through-hole penetrations though the electronics protective sleeve may be provided without departing from the present disclosure. If an electronics protective sleeve is not used, this area may be used to directly mount other systems or components of the container locker. In other embodiments of the present disclosure, the systems or components may be housed in other areas of the container locker. Connections from devices housed in space 19 to other parts of the systems operating in the container locker may exit the sleeve or areas where situated through through-holes 19A or other engineered or designed through-holes drilled through the sleeve and/or the sidewalls to allow wiring to connect to other devices, appliances, wiring harnesses 13, 17, 20, and other wires or harnesses or internal wiring connections. Accordingly, repairs may be made by isolating certain electronic devices enclosed therein.

Modular electronics housing sleeve or installation/mounting area 19 may be used for the modular electronics housing sleeve insertion and holding or electronics installation and mounting area and/or interstitial area for the mounting of electronics, components and other operative devices. Sleeve/area 19 may support one or more of the systems used in the operation and functions of the container locker, including, but not limited to, one or more single-board computers, and including other devices, drivers, components and appliances or portions thereof used in supporting or operating on-board and networked forms and the functions and operations, among others, related to: communications, GPS or other positioning or locational operations, gyroscope operations, weight tabulation and weighing operations and functions, temperature controlling and related cavity cooling or warming equipment operations and functions, cellular telephone functions and operations, wireless and hardwired networking operations, programming operations, drone or unmanned vehicle communications, operations and functions, locking, unlocking and other security mechanism drivers or equipment and their functions and operations, camera and video functions and operations, lighting functions and operations, notification and status functions and operation, barcode scanner components functions and operations, or, photo and video drivers or equipment functions and operations, speaker and/or horn or siren and microphone functions and operation, motion sensing, lighting, antenna, solar collector, lid opening and closure, autonomous container motorization, battery, weighing, audible or visual security and other related on-board 4G and 5G repeater relay devices and network connected system actuation, functions and operations. If in the modular embodiment anticipated, sleeve 19 may be inserted into the form-fitted interstitial space designed for it. Quick-connect wiring and connectivity through-holes 19A may be used for wiring and connectivity to connect electronics in sleeve/area 19 to other parts of the container locker where other operative devices, appliances, and systems reside. In a modular embodiment, sleeve 19 may be quickly disconnected using through-holes 19A, removed, replace and quickly reconnected as a convenience to service and repair representatives troubleshooting and or fixing broken or non-working aspects of the container locker.

FIG. 5 depicts a view of the sub-floor of cavity 9 of the container locker of FIG. 1 according to an embodiment of the present disclosure. This insert or sub-floor may generally be solid and unibody in form as well as protective and durable. It may create a generally user-inaccessible interstitial space area below it, between it and the container floor and, which simultaneously creates a floor for cavity 8 above it.

Figure 6:
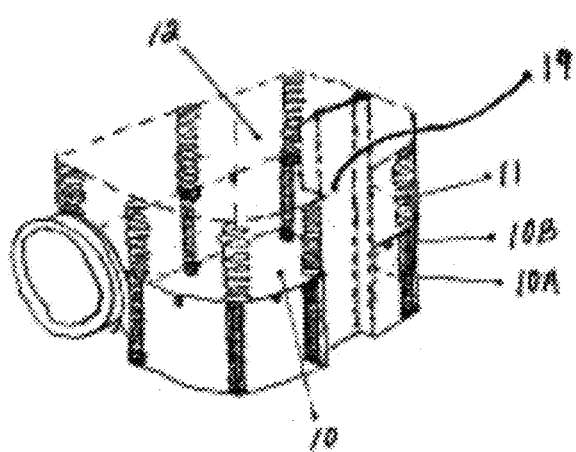
FIG. 6 depicts a view of the middle layer of cavity 8 of the container locker of FIG. 1 according to an embodiment of the present disclosure.

FIG. 6 depicts a view of the middle layer of cavity 8 of the container locker of FIG. 1 according to an embodiment of the present disclosure. This area's ceiling may serve as a spring loaded or floating floor for cavity 5 above using its springs, netting, or other cushioning materials suspending it in place which cushions the blow to the contents in parcels as they are dropped into cavity 5 as discussed above. Additionally, this ceiling also may serve as a scale deck working with collocated digital load cells, mechanical scale equipment, and/or computers and electronic devices and systems located either in cavity 8 or interconnectedly with other scale parts outside of the cavity that assist in the tabulation, recording and data transmission related to weighing contents as they are placed into and/or taken out of cavity 5 above it.

FIG. 7 depicts interaction between a container locker according to an embodiment of the present disclosure and an unmanned aerial vehicle or similar device. The container locker may include automated capabilities to interact with an Unmanned Aerial Vehicle (UAV) 31, drone-drop, and/or other machine or mechanized forms of delivery such as but not limited to a delivery robot or other autonomous vehicles, in the process of receiving into or sending out parcel 32 from the container locker. The UAV or drone may be programmed to work directly with the container locker and may be sold as an ancillary or acoutremental additional part and be housed (or docked) with the container locker or the UAV may be owned and operated by others and be programmed to communicate and interface with a container locker. In both events, the container locker can communicate with the UAV to make deliveries into the container locker or to send back out return items to their origin.

UAV 31 may deliver or pick up parcel 32 to provide an automated, safe, secured drop zone or place for UAV 31 to drop its delivery cargo regardless the presence of people involved in the delivery. Other forms of robotic delivery means and modes can likewise connect with, communicate with and utilize the container locker to perform delivery and retrieval functions and operations if so configured and/or programmed to do so. As used herein, parcel 32 may be a package, box, bag or other item that is delivered to or retrieved from the container autonomously or with the aid of people using manned or unmanned means of accomplishing those delivery or retrieval tasks.

In UAV deliveries, the on-board computers and integrated communication, GPS and other systems of the container locker may engage the UAV's wireless signals or vice-versa when in range of each other and will wirelessly sync communicatively with each other to position the UAV and ready the container locker for access. As the delivery vehicle and the container locker connect wirelessly through their on-board systems, the on-board system of the container locker may direct the unlocking of lid 1 using its integrated circuits in magnetic locking system 18, and may open lid 1 using electrical motor(s) 3 and hatch opening gear 2 retrieval or placement of the good. Once UAV 31 is centered in an appropriate drop position hovering over the top of the container locker, using wireless communication systems 19, GPS 19, cameras 28 (and other cameras) as interconnected with UAV 31's on-board communication, GPS and camera systems, UAV 31 may maneuver and drop parcel 32 into cavity 5 of the locker. As this is occurring and after parcel 32 has landed in cavity 5, data will be exchanged wirelessly between UAV 31 and the locker's on-board systems 19 or others and some data will be transmitted to parties interested in the delivery or retrieval via their on-board systems or other remote systems interfaced with the locker's operation. Once UAV 31 or other unmanned delivery vehicle is hovering, or otherwise situated in physically proper place nearby and within communications range to make the delivery or to retrieve contents in/from the container locker, UAV 31 and the container locker may communicate with each other wirelessly and transmit several different forms of information between each other using their independent on-board computers, electronics, protocols and software signals. Data communicated and exchanged may include, but is not limited to, (i) the confirmations of GPS locations and addresses used in the order placement, (ii) confirmations regarding the order be delivered or retrieved, (iii) the granting of permission to access the container locker, (iv) the willingness to access the container locker to drop or retrieve a parcel by UAV 31, (v) the weight of the parcel being delivered or retrieved, and, (vi) various other information relative to and important to the payload exchange.

Generally speaking, the wider and less obstructed the opening is for delivery into a container at its top, especially when a parcel is being delivered by a UAV 31 drone-drop type system or other type aerial vehicle, the more likely a successful drop will be able to be made by a drone or other automated delivery mechanism. Hovering as close to the actual drop site is important to the drone as it lowers to place (or drop) its delivery into the locker. This capability to provide this type of totally open orifice for loading and unloading packages lends itself to many of the types of roll-out trash container and other containment systems types of designs and products in use today throughout the world and those familiar with the industry plastics manufacturing would recognize the ease with which same can be acquired or made with specific purposes in mind.

As discussed herein, the container locker may use GPS technologies to assist in determining its whereabouts at any given point of time. GPS may include a single GPS receiver or transceiver 16 and 19 that receives signals transmitted by GPS satellites encircling the earth in low-earth and other varied earth-orbit altitudes and transmits data to location finding servers or receivers to triangulate its position. Receiver 16 as processed through 19, may be in constant communication with a network of these GPS satellites and can relay, wirelessly or otherwise to its user through the system. Based on the GPS satellite's transmitted signals, the receiver may determine its own position and, resultantly, the user of the GPS unit can determine its position with a nominal margin for error of its exact location anywhere in the world for delivery and retrieval personnel and apparatus to isolate its location for use. The container locker may be configured with, outfitted with equipment and software for and interact with alternative types of GPS systems 19, wherein the GPS system may provide the ability to monitor and track one or more remote units in one or more central location(s) and where they may also be used to collect, remotely store, transmit and/or analyze the data from the central location(s) and where the locker uses GPS data, as well as other types of data, to ascertain the current, as well as past locations of the remote units may be used as well in locating the container locker and in verifying the current address or location of the container locker at any given point in time. In alternative embodiments, the GPS locational system and/or other onboard systems may also be extended for use in other location-determining applications wherein it may use a honing geo-locator device operating through 19 and fixed at a specific location to determine the proximity (distance) that the container locker is situated to it relative to that fixed or given designated location and the physical location of the container locker at the present time. As an added benefit to the user, in the absence of a broader GPS integration, the device may have a wireless or hard-wired module which contains receiver or transceiver that emits a signal which is fixed at a user-determined location that pings a signal to the container locker and an onboard receiver/transceiver which reads and/or processes such signal to geo-locate the container locker, relative to the fixed point of the signal's origin. Other on-board or remote computer systems and software may process the data transmitted between the two devices to determine and express via wireless or other communication to the user physically where the container locker is then situated relative to the signal being sent by an onboard container locker embedded transceiver, identifying and communicating its locational aspects.

Users may be provided a means to capture, store and transmit data with the specific locational information where acts involving the locker have occurred and delivery retrieval personnel or UAV drone can perform the task with the locker serving as the party's depository. Embodiments of the present disclosure may allow one to document the actual time, weight and locational aspect of where a delivery or retrieval (pickup) has occurred through use of on-board GPS systems 16, 19. Confirming the specific location is especially important when verified through computers 19 and scanners and ability to connect to scanners through USB Ports 14A, 16 and 19 or other interconnected means. When scanning, the systems and appended device connectivity may provide the ability to confirm that a package with a specific UPC label, as scanned, was actually at the location of the container locker at a specific time and physically situated at a specific location, that when it entered or left cavity 5 and was weighed (or otherwise its absence weight-wise was tallied) that it weighed a specific amount and that the other data, photographically and otherwise verifiable through measurement by the container locker systems, can justifiably document that a delivery or retrieval or other action did occur at the recorded specific place and time and verified by the weight placed into or taken out of the container as documented by the transmission. Tracking may be provided through GPS means, tracking module and/or GPS locational software run on local computer 19 and systems integrated therewith that will not only allow the owner/user to verify the locker's location through its accompanying smartphone or computer 19 digital software application (via the use of an App (software application specifically designed to interface with the locker), but which will also deter would-be thieves from attempting to relocate the locker and its contents from the intended location chosen by the owner/user. Should the locker be removed beyond a certain distance, anticipating 3' or +/−1 yard in distance being the anticipated "ground-zero mark for the container as placed by the user, from its intended location as set by its owner/user, the embodiments with this feature may also have a security-redundant high-decibel audible alarm and or flashing lights 20C that become triggered to indicate to others that might hear such alarm that the locker is being removed (and perhaps stolen) from its intended placement location. In addition to the flashing lights on the side of the locker's exterior, other operational lights and or sirens, horn or alarms may also be activated in such a case. These features, if integrated with the user/owner's other security system(s), may also integrate with and trigger other alarms, lights, cameras computer systems and systems to alert the authorities that the appliance is being tampered with, has been tampered with and or at minimum, is in jeopardy of being broken into, breached, stolen, or is being stolen. If a thief cuts the security tether with a pair of bolt cutters and steals the entire locker and throws it into the back of a truck or van in order to steal the contents of the locker that he/she may have seen placed therein, the piezo-electric sounder, once removed from its user registered GPS location at 100 decibels or louder.

In some embodiments, the container locker may be outfitted and its system integrated with a motion, pressure or other types of sensor(s) or other gyroscopic component(s) designed to recognize an unusual or unanticipated motions, pressures, temperatures and/or movement of the device which would be integrated with and operate through computers and internal systems 19, like, a shaking, jarring or other undesired physical control aspect of the locker. Wherein such undesirable activity occurs, the system may trigger the communications dispatch of data or other information to other onboard parts of the system or computers via a the system's internal or external integration with those other systems, devices or apparatus' to broadcast a high-decibel audible alarm of varied types, cameras 15 and 28, sirens 19B and 25B, and lighting 4, 20B and 20C and, if integrated externally with the owner user's security system, may trigger one or more external alarm systems to perform the intended function of alert nearby persons to the event and/or to alert or otherwise digitally or wirelessly alert the sheriff, police or law enforcement authorities, and others that the locker has been materially tampered with, moved or is currently moving (as in a truck or van when stolen), knocked around or materially bumped as it would in the event of a thief or thieves might be attempting to carry it to a vehicle and away from its user/owner's intended placement location. In addition to alerting nearby persons that can hear the alarm sounds, and the police to this, the system 19 may also be configured to alert or otherwise notify the user/owner of the device wirelessly through connectivity to the internet, IoT connectivity to other devices, the accompanying smartphone computer or smart pad App and other communication systems that the locker is, or may be, was or is at risk in some way.

When applicable, a container locker according to embodiments of the present disclosure may use a wirelessly or hard-wired, attached or built-in cameras 14, 15 and 28 or another similar configured connected or portable device attached through USB connectivity portal 14A as an on-board scanner device detection to either to scan the parcel, package, item or ticket that follows the order from its origin to the container (or, in the event of a return (i.e., a retrieval) a receipt and/or other ticket verifying, pursuant to the agreement between purveyor and purchaser, that the items are callable for return. Wirelessly up-linking the scanner through the locker's onboard computer 14 and 19 allows the sender to be provided video and/or photographs of the personnel engaged in the process of delivering a parcel(s) and confirm the safe re-securing of the locker after specific data on the parcel being delivered is read by a scanning device, such as a camera or other scanner and the unit is resealed and secured. The scanning apparatus used in conjunction with its wireless integration with computer system 19 and software designed for same which would drive it, may be used to scan the UPC label of the package(s) delivered in lieu of additionally entering a security code through comm-center 14, to electronically release the locker's locking mechanisms which would otherwise prevent unforced access to the delivery or pickup cavity area or area(s) 5 and 27. Embodiments may use a proprietary software and/or may use a vendor's specified or open-source software interface to communicate and receive and/or transmit information regarding the parcel, package item or ticket related thereto to interested parties to the contract of sale transaction related to the specific item(s) and the related delivery or pickup service which also may include configuration with one or more cameras 15 and 28, other on-board or portable handheld scanners through USB connection 14A, wireless or hard-wired receivers, transmitters or transceivers and/or other components housed in or on the locker to confirm or maintain security in the delivery or retrieval task and to provide for the confirmation and/or digital proof to the interested parties that the required delivery or retrieval task was, indeed, completed or performed.

The container locker may be hard-wired connected to a network through its USB and Ethernet Connectivity Port 14A, and/or may be wirelessly connected to a network through its electronic computer 19 and/or other on-board antennas 16, transmitters, or receivers (transceiver(s)) component(s) and computers 19, its USB or Ethernet Connectivity Port 14A, and may connect through such wireless syncing directly, through cellular protocol, through Bluetooth 19 and 16, cellular or similar connection, or through other means or protocols used in digitally connecting communication and other devices. Communications may take place wirelessly through digital wireless protocol connectivity to a user's home or office wireless network to integrate it with other digitally operated communication systems. Functions being performed in receiving deliveries and pickups from delivery services manually or in unmanned means may automatically trigger messaging, photographing and other data collection, transmission and recording to be sent to interested parties in order to alert and or confirm to them that the delivery or retrieval has occurred, that the locker is secured again and or to send visual or other records to confirm that the delivery or retrieval task was completed at a specific time date and, in some cases, that a specific weight tabulated and recorded through on-board load-cell and scale assembly 8 and through computer software and system 19 has been placed into or taken out of the locker once completed. On-board communication systems 19 and 16 may use varied text, cellular, wireless linking to email, and a multitude of other forms of digital communication, as configured, to provide information to the deliverer, the sender of the parcel (purveyor), the recipient and other interested parties to verify and ensure the interested parties with data that confirms when a delivery is about to occur, is occurring and/or has occurred providing, depending on the needs of the parties including transmission of a variety of information to all related parties of these events and other information or data as set forth in the agreement(s) between the parties for such delivery.

A set of electronic contacts may be included at an accessible position on the lock housing to allow both master access and power jumping with a common manager's implement, for situations of lost codes and/or battery 27 failure. In particular, lid 1 lock may be long, narrow and low in profile so as to fit into the predesigned spaces set out in the locker's design to contain locking mechanisms 18, wiring and necessary operational hardware throughout the locker. Similar to USB ports in a computer, like a laptop or desktop computer, the electronics contact hub of one or more USB connection ports 14A may be situated in a conspicuous easily reachable location on or near communication-center keypad and display screen 14 which may be used for a wide variety of purposes such as, but not limited to, computer/wirelessly jumping for the repair, re-coding and the re-boot of systems through software interface and connectivity through it, as an external connection port to access the locker's on-board computers and electronics for additional programming, manipulation and settings manipulation, repair and/or to set up computers and peripherals 19, cameras 15 and 28, weighing scales 8 and weighing equipment 8, and other on-board equipment, computerized equipment, devices used in the operation of the locker or otherwise connected to it, to charge other devices connected to/through it.

Software operating on the locker's computer(s) and or devices may enter a recovery mode in the event of a crash and communication-center screen 14 may be used in conjunction with another computer or wireless device, like a smartphone, through an App (application) to re-set the on-board computers and systems that are either wirelessly or hard-wire connected.

Scans and or the scanning of the parcel's UPC label may also be accomplished through an encrypted wireless signal to the parties interested in the parcels' delivery confirmation. This device and system may use the internet, cellular, texting, and/or other IoT connected means to deliver the information in order to verify the safe completion of the delivery of a parcel(s) to a specific location at a specific time. The system and method may transmit or receive a timing date-stamp and other useful data, including, but not limited to, photographs and video of the delivery event itself and can also, through a transmitted scan of the parcel's UPC labels or other types of labeling on the package surfaces or otherwise accompanying the parcel, can confirm delivery of the parcel or item to the recipient back to the sender thereof and/or to others specified in order to confirm that the delivery has occurred at the prescribed location at a particular time. This particular form of confirmation is important to the sender of the parcel to not only provide access to an area otherwise inaccessible, but also to confirm that delivery or a retrieval were, indeed, made, and the precise time of delivery or retrieval. It is also particularly important to the recipient or others interested in the process to become aware that the delivery or pickup of his/her parcel has verifiably occurred, and photographs of the parcel in the locker, the confirmations of the unique UPC and the parcel's weight when delivered may serve to confirm this. The locker according to embodiments of the present disclosure may also have additional efficacies for these processes or ancillary utility in the general use thereof given its interconnectability with other systems and its typical intended placement proximate one's home or office and interface with and connect to their related wireless or hard-wire connected systems.

As depicted in FIG. 8, a multitude of alternative shapes, sizes, materials, and other features may be included as part of the container locker according to embodiments of the present disclosure. Exterior 29 may be stainless steel but may be constructed from other similar materials without departing from the present disclosure. The container locker may be dipped, coated, extruded, molded, roto-molded, welded, or otherwise assembled or put together using a myriad of types of materials that would logically lend themselves to and be suitable for such construction. Materials may include plastic (FIGS. 1-3), metals such as stainless steel or copper (FIG. 7), or combinations thereof. Impact and corrosion resistant materials including, but not limited to, high density High-Density Polyethylene (HDPE), Polypropylene (PP), Polyvinyl Chloride (PVC), Low-Density Polyethylene (LDPE), Polyethylene Terephthalate (PETE or PET), Polystyrene or Styrofoam (PS) and/or other miscellaneous plastics (such as: polycarbonate, polylactide, acrylic, acrylonitrile butadiene, styrene, fiberglass, and nylon and others) plastics may be used and be reinforced at stress points for durability, and may include a hinged or sliding, tight fitting locking lid(s) and handles to protect and secure items placed inside, and would easily be tilted backwardly and rolled to provide mobility and portability using a built in grip handle and a multitude of various types of axle-mounted wheels 7, 21, which may be 7½" to 12" diameter.

In some embodiments of the present disclosure, the container locker may be fixed in a specific location, such as a segregated and secured area of a residential subdivision, on a rooftop, on a floor of a building interior or a combination thereof, either independently or in an array of multiple container lockers. The term for this type of facility is coined as a DronePort™ and/or a DronePort Terminal™. In this arrangement and configuration, several or many container lockers, often having a variety of different features, may be arranged open to the sky above, in groups, side-by-side and in segmented rows in a secured and gated exterior area. Interior locations also can be provided wherein multiple locker containers can be situated in a centralized area where delivery personnel and users, alike can access them. When communally nestled together in one area, the container lockers can be specifically designed as an on-site facility near groups of users that would access them. The "DronePort™" may serve as a central nearby location established to be accessed by a group of users, delivery people and machines. In this communal configuration, like a residential subdivision, this small security-gated area houses multiple devices in one central location where drone deliveries and or manned deliveries, alike, can easily be dropped and securely stored until the user desires to retrieve them. This also permits purveyors of goods making deliveries to go to "one" central defined drop location for deliveries to the area, saving them millions in fuel, wear and tear on their equipment (and their drivers) and, most importantly, prevents deliveries from sitting on one's porch or doorstep all day tempting Porch-Pirates while the homeowner is away. This may be installed as part of a subdivision or commercial property as it only needs a small section of land or interior space in the common areas of the subdivision, building or area serving the users and estimated area sizes range from a few hundred square feet for a small project to several thousand square feet for large numbers of users depending on the number of users and can serve in residential, office, retail, industrial and other types of communities of, both, residential and commercial locations and applications.

FIG. 9 depicts a layout of a scalable facility according to an embodiment of the present disclosure. In this embodiment, an 80-unit DronePort terminal may be provided to serve a residential subdivision and may be situated in common areas of the subdivision allowing deliveries and pick-ups to be made at a central location. Drone deliveries and/or manned deliveries may be accommodated, and users can easily use the facility and their individual units to securely store returning items for manned or unmanned delivery personnel to retrieve them. While a specified number of units are provided in FIG. 9, it should be appreciated that more or fewer units may be provided without departing from the present disclosure. These units may be arranged in rows and/or groups (segments) in embodiments of the present disclosure. The rows and/or segments may be common linear groupings to permit easy pedestrian maneuvering. Typically, approximately 10 units in a row may provide a segment. It should be appreciated that the units may be provided in different sizes as some packages may be too large for placement into the typically sized container locker or a container locker may from time to time be out of service. In these cases, oversized lockers may be provided at various logical locations inside of the controlled areas of the DronePort™ so that delivery personnel can still make deliveries to people whose locker cannot accommodate receiving a larger package or where their locker is out of service. Parcels or items delivered to an auxiliary overflow locker unit can or would typically be used on a temporary basis and can communicate that such has been made to an alternative locker and location through the existing communication systems.

The DronePort may include a concrete floor area or other hard surface material (like macadam or black-top) generally used in the out-of-doors poured and finished over the pre-designed under-slab electronic, communications, drainage systems lines and other items typically laid thereunder. Typically, power and communication lines, as well as drainage and other items needed for the operation of the DronePort can be installed in conduit chases underneath the slab. These conduits can be used to run or pull wires from mains power sources such as an electrical panel, communication hubs, such as a router or other access-controllers and other controller panels like security, lighting and the like. These lines would typically be stubbed up at the appropriate location to be extended out of the slab, into the operative device and used to connect and operate individual container lockers, security and access control systems, lighting, and other needs of the facility. Each individual container locker may be connected to power sources, other communications panels and/or other integrated systems protruding through the slab at the bottom of the location where it may be permanently affixed to its location using bolts and or other means to cause it to be irremovable. Security cameras may be provided throughout the DronePort to provide security to its users, record happenings in the space and to permit those contemplating entering the area the ability to see at the control panel who may or may not already be in the secured area making it easy, safer and/or more comfortable for users to gauge whether or not they care to enter the secured area at the time. This also may allow security personnel and/or law enforcement to check the inside area(s) from the visual access control panel outside of the area without entering same. Camera footage may be recorded for future use in the effort to promote security and safety for users. A security fence may surround the edges of the concrete floor. It may be 8' high or taller chain linked fencing construction with cantilevered apertures extended from the top thereof to prevent intruders from being able to scale the fence and enter the secured area. Dusk-to-dawn or motion-sensing lighting fixtures may be provided that may be programmable through the on-site security systems and/or automatically triggered by light-sensors to provide adequate lighting of the DronePort areas for its users in dark, darkening or nighttime periods of time to promote safety and usability of the space in evening and at night. The access control panel may be a visual panel outside of the secured area which may be hard-wired and/or wirelessly connected to a controller and system hub to provide the selective restriction of access to the DronePort area(s). As a secured area with a myriad of valuable goods and items temporarily stored in the container locker units inside, restricting access to user members only is key. This may allow persons with a container locker to gain access to the area that securely houses the container locker itself and may be indexed by residential address, telephone number and/or myriad other criterion to promote security and safety of the access to the area and, ultimately, access to their specific container. The DronePort may include a security access-controlled gate, door, and/or opening that may be controlled through the access control panel. Such gate may be automatically driven by a chain or other opening/closure mechanism and may be triggered to open for a limited period of time when the appropriate code is entered into the system at the access control panel. To exit the internal DronePort area(s), an electrical system-controlled button and/or panic-button on the inside of the contained area may be provided to open the gate for users when they would like to exit the area(s). There may be a power and electrical panel source that provides power and other feeds to the security, lighting, access and other systems requiring electrical power to effectively operate. This electrical panel can be secured by placing inside "or" outside of the secured area(s) as needed and can be independently secured with fencing or other forms of physical or placement. This power source location may also house or be in or near other access, security or other systems serving the DronePort facility. The DronePort facility may include grounds landscaping directly outside of the security fencing to beautify the DronePort facility and to inhibit intruders from climbing the fence as added security.

Embodiments of the present disclosure may deter and/or decrease dishonest delivery personnel. Using cameras, especially internal camera 28 of cavity 5, the parcel may be weighed with on-board scale system 8 when it is placed into the container locker with scale system 8 and confirming and/or tabulating other data regarding time via on-board computers 19, date and information of other importance to the task of delivering or retrieving. Through the use of its on-board load-cell and weighing system 8, the container locker according to embodiments of the present disclosure may scan, tabulate, communicate and confirm to the delivery-interested parties through the system's communication means provided through the use of the array of parts to insure that, among other verification data, the weight of the parcel when weighed at its outbound origin is the same as it weight tabulated at its destination when it is received. This may provide a concise and complete confirmation that what left the warehouse was actually delivered which is not yet widely used and herein is able to create, yet, another level of accountability through this weighing. Further, using the weight of a parcel, when weighed at both origin and destination, may allow for the avoidance of tampering with packages, parcels, bags and items in transport and/or prevent the theft of one or more items that may been shipped together in the same package, parcel or bag. This may avoid delivery piracy and may be tremendously useful in deterring the delivery personnel from even beginning to believe that he/she can steal any part of a parcel while in transit and can serve as a material stop-check for merchants, purveyors, customers and delivery service enterprises, alike; one that will be welcomed by corporate accountability and theft prevention staffs as it becomes deployed.

Embodiments of the present disclosure also confirm for the merchant, purveyor or distributor who sent the parcel by accounting for the weight of the parcel when it left their facility is either the same or different when it has reached its intended destination. With an urban delivery driver making 160-200 stops per day and delivering an average of 200-300 pieces to location along their route, there is a lot of room for error and, for some, much temptation to sneak a little something for him/herself along the way. Using the container locker according to embodiments of the present disclosure, if a 5 lb. parcel with 4 items in it left the distributor's dock as a 5.0 lb. parcel, it should weigh the same amount (i.e. 5.0 lbs.) when it reaches its intended destination. If it reaches the container locker and is measured at 3.7 pounds, all parties can immediately recognize that something is awry and that the parcel was lightened by 1.3 lbs. Accordingly, it may be possible to more quickly be able to identify what item(s) had left the dock in any given box or bag, but which had not actually reached the intended recipients when placed in the container locker and weighed. Further, embodiments of the present disclosure may tabulate, communicate, and confirm that a parcel, package, bag or item of a specific weight associated with such parcel, has actually been placed into the intended recipient's container locker for delivery while also confirming the UPC label associated with the parcel to double-check that its weight is actually what left the warehouse when initially weighed and labeled. Moreover, a photograph or video of the delivered parcel may be taken with external fish-eye camera 15. After the package is secured and the system has closed lid 1 and the contents are secure in cavity 5, internal camera 28 can again photograph the delivery or the absence of the item taken for return and may forward such photographs to the parties interested in the confirmation of such delivery. Embodiments of the present disclosure can confirm in several ways, for all parties involved, that the parcel leaving the DC (distribution center) weighing a specific amount and due on a specific day was actually delivered and placed into a verifiably secured location.

At initial set-up, the user (owner or operator) of the locker may program the computer electronics to recognize one or more personalized identification means, such as, but limited to, voice recognition, punching numbers into a keypad bearing digits, symbols or alphabetical letters (hereinafter referred to as a "PIN #") or other numeric, alphabetical, thumb or fingerprint for biometric identification, unlocking key or other code, iris (eye) or facial recognition or alternative identification code or other alternative security means or protocol or means wherein such user may, at will, grant access to others at his/her discretion and pursuant only to his/her permission or the granting of such rights of access to the locker to others. Some embodiments may use multiple different and/or separate recognition protocols for different deliverers, merchants, purveyors and/or purposes in order to provide the specific grant of access based on a certain specified protocol agreed to between the user/owner and such other party and where such specific party may have the right of access for a specific reason or period of time as configured by the grantor of the rights of such access to that other party.

The container locker may be connected to, whether wireless or through hard wire, and integrated with the user's home or office security system network through the locker's computers 19 and antennas 16 and/or through similar onboard means housed and operated from the locker. In this integrated or connected condition, the systems of the container locker may, through such connectivity of the security system's protocol components, devices and/or design, be considered and extension of the user's home or commercial security system. In such connected configurations, it may be operated as a node of such system wherein an attempted breach or breach of the locker systemically communicates and notifies or otherwise alerts the then integrated systems through the sending and reception of data transmissions related to same. In such an event, the breach or attempted breach may trigger other aspects of both, on-board and other connected security system actions such as, but not limited to, setting off on-board or remote audible or visual alarms, on-board or remote lights notifying police, security personnel or others, on-board piezoelectric sounders 25B, speakers 19B or other sounders situated remotely. One familiar with the art would understand that based on as set forth in the security system's setup, design and adoption by the users thereof, a myriad of possibilities for alarming and alerting when combining two separate security systems. Those having skill in the art will also recognize that security systems in the current age have remote wirelessly connected devices that are integrated thereinto and the locker may possess a similar integration, as if it were merely a seamless addition to such a system in order to have it perform its alarming, notification and other security functions.

The locker's electronic heating and cooling systems and apparatuses may be housed or extended into cavities 5, 8 and/or 9, regardless the type employed, may operate as a self-contained battery powered heating or cooling container and/or may utilize a common 120-volt AC power feed (source) across its low-voltage PCB to operate and to charge other on-board batteries simultaneously. Other embodiments may also utilize an on-board low-voltage battery or batteries 27 as a back-up power source, such as a common 12-volt rechargeable battery 27 to operate the locker, or, via connectivity to an off-board low-voltage power source system (jumped from another source) like that of a common car or truck battery, like the common and typical battery and system found in a common or typical automobile, to power its functions normally while connected, and in order to recharge its on-board system(s) or in the event of a power failure, a loss of power or a change in the user's ability to access power or otherwise where it would be necessary as a back-up or redundant alternative as a power source. Cavity 5 may be capable of providing refrigeration and/or warming capacity to maintain temperatures in order to prevent the spoilage of groceries, food, medicines and other temperature sensitive materials or items.

While the locker may be scaled upwardly and downwardly in size and dimension, in some embodiments, generally, it may measure volumetrically at approximately 65 gallons, which generally may provide dimensions of approximately 28" (Length)×28" (Width)×45" (Height) to create an interior space in the 65 gallon size range and to provide enough room in cavities 5, 8, 9 to perform their multiple intended purposes and functions. This size would provide the users with the most flexibility and benefit while still maintaining critical portability, maneuverability (if in a portable embodiment) and access to the indoor or interior spaces of one's home or office through normally or typically-sized doorways or points of ingress and egress to a structure like a typical residential home doorway.

The locker according to embodiments of the present disclosure may commonly be used and stored in one's garage and or in and around one's driveway or garage and home front or backyard door area(s). Thusly, such embodiments also may include both high reflectivity exterior surfaces or areas of such surfaces and embedded glow-in-the-dark features 6 to provide benefits and utility to both the owner/user of the apparatus and delivery personnel accessing it in dark hours or settings. As referenced elsewhere herein, as the delivery of parcels, packages, bags and items become more and more mainstream to the home for any given person or family, the hours of such deliveries are anticipated to be extended as well into nighttime hours wherein a delivery person can navigate the roadways infinitely more expeditiously and free of congestive traffic in most urban areas today. Given the ability to marginally decrease drive-times and also to drive out overhead costs for labor and other aspects of operating delivery services by delivering goods in "off-hours," night-shift deliveries are anticipated to grow extensively and quickly and will become larger and larger parts of the logistics processes for most purveyors whom desire to get goods to their customers quickly with less traffic and timing friction. Thusly, with the use of the locker according to embodiments of the present disclosure, nighttime deliveries may grow as rapidly as needed driving out delivery cost for purveyors; given the locker's ability to be accessed regardless the intended recipient's absence or presence at the delivery location and its ability to secure deliveries made in a controlled environment until the recipient is ready to unload the locker. This means that nighttime deliveries of items can easily be made, f/b/o the intended recipient and the delivery personnel or company, with the use of this locker while the owner/occupant slumbers. Dark hour delivery personnel may spot the container locker quickly in dark or darkening settings as they approach the delivery location with the intention of making a nighttime delivery.

Wheeled trash cans, and other items often clutter a garage and/or a driveway and backing out a car from the garage can quickly destroy those things unseen by the driver and verily run over by him/her as they exit the garage in reverse. The high reflectivity and the glow in the day features of the rugged outer shell material aids those using the locker in not damaging same accidentally as it sits in locations often designed for vehicular traffic in and around the home or small office driveways and automobile access areas.

The ability to place logos or names or other branding on the sidewalls and top of the locker are not to be unrecognized. Although not illustrated in the figures, the sides (and or tops) of the locker may bear markings such as corporate names, logos and other messaging for public view, not only of the manufacturer thereof, but the purveyors, retailers or other sponsors and users of the locker that might engage in sponsorship or other marketing efforts that can plausibly utilize such an area to enhance or otherwise grow their brand recognition and branding in general.

Various examples are provided as described below. In a first example, Annette, a resident of a suburban area in Royse City, TX, purchases a 30-pack of her favorite Keurig k-cups coffee online from a major online purveyor of goods. That evening, in a mad rush, her boss orders her to fly out immediately to the companies' Wichita office for business where she will need to stay for at least 4 days to address critical issues there. In embodiments of the present disclosure, both the purveyor and the buyer can follow through with the delivery/reception of her newly purchased coffee into the container locker in her absence with a high level of safety and security with verifiable photographic and digital data evidence that the delivery was actually completed and delivered while she is away at work and it has been protected in the locker since delivery. When this delivery was completed, she received a text and an email with photographs of the delivered parcel inside her locked container which was directed through the seller's delivery software and the connected container locker to confirm and verify that the delivery was been successfully completed at 2:05 PM on November 11, and that a 2.9 lb. package of coffee had been placed in her container locker by D. Sanders, whom she knew to be her usual delivery person. While away, she can peer into the locker and surrounding areas in her garage to verify and see that the package was left and that it is secure through use of her smartphone App as well. Given that Annette is keen to porch pirates operating in her home's area lately, she did not want her container locker on the porch all day after her delivery was documented on her cell phone and computer, so, Annette used her cell phone app to relocate the container into the garage. The interconnected wireless systems on-board allowed her to open her garage door, drive the container locker into her garage and automatically triggered the garage door closed after relocating to the predetermined secured space inside her garage. When she returns from Wichita 4 days later, she can retrieve her coffee which has been secured in the locker in the garage without being exposed to porch-pirates, the weather, or other detrimental effects of sitting outside on her porch, and without disruption to her neighbors or others that would have had to pick up the parcel when delivered to her doorstep or otherwise received or held the delivery until her return.

In a second example, a new drone-drop delivery service is employed by a local urban pizza shop in Austin, TX to use UAVs to deliver pizzas to customers ordering and paying for their pizzas online. Shortly after placing his order with this pizza shop one cold winter's night, the customer that ordered pizza was called to a neighbor's house for a serious emergency which takes several hours for him to assist in helping to address. While at his neighbor's house, he can use an app on his smartphone to set the temperature of the locker to keep his pizza warmed after delivery in his absence. Accordingly, the man's pizza can not only be received by the unmanned drone-drop service automatically, but video and or photographs of the delivery can be verified along with the transmission of various other data regarding the delivery to interested parties, the contents can be warmed while he is gone, and this can all be accomplished automatically while he is away attending to urgent matters at another location. When the customer returns from his neighbor's house, he returns to open the locker to retrieve his warm pizza pie.

In a third example, Michelle, a lady in Lubbock, TX, orders three items online on a summer day from a major online purveyor of goods: a swim floatie for the pool, chlorine tablets for her pool, and a large bottle of sunscreen. The package is 'picked' in the purveyor's warehouse and placed in one box sized to contain all three that has a total weight of 3.0 lbs and the parcel's UPC label indicates this total weight. The floatie weighs 1.5 lbs. The chlorine tablets weigh 1.0 lb., the big bottle of sunscreen weighs 0.40 lbs., and the box that contains them all weighs 0.10 lbs. Collectively, all items and the packaging weighs 3.0 lbs. including the box containing them. Michelle receives the package two days later only to find that the sunscreen is missing. The box is also opened at one end. She calls the purveyor to figure out what has happened. Since the package was delivered to the container locker, there are records associated with the delivery including time, date and weight of the parcel delivered and who (the person or machine) that delivered it, including video and or photographs of the delivery taking place, a digital record of the delivery person(s) that accessed the locker during the time in question, and the photos of the parcel inside the secured container area after delivery and lock-down of the lid afterward, all of which can assist Michelle and the purveyor sender in assessing what next steps should be to make Michelle and her husband happy and to alleviate her husband's propensity to get sunburned when in her pool. In this example, the total weight of the parcel, 3.0 lbs., is the most useful. The locker's computer components indicate that only one access was made into the cavities leaving only 1 parcel on the day in question, that parcel "should have weighed" 3.0 lbs., and it was placed in the locker at the exact same time that digital records indicate that the purveyor's deliverer executed his delivery prowess at the locker. However, the parcel indicated on its label that the parcel weighed 3.0 lbs. when it left the purveyor's distribution center. They can now deduce that the sunscreen was in the box when it left the DC, but for some reason never made it to the customer. Had either one of the other items, the floatie or the chlorine tablets, been the missing item, the weight tabulation at the delivery-end would have similarly identified "it" as what did not reach the customer instead. The purveyor's internal loss prevention specialists were able to ascertain over a short period of time that it was more of a specific 'route' problem and moreover, was related to this particular individual driver, and the chronic complaints of recipients situated on his typical delivery routes. This gave the purveyor the comfort to investigate the pilferage matter and immediately dispatch a replacement bottle of sunscreen to Michelle. Needless to say, the information validated and gathered through the locker made it easy to identify the culprit with verifiable proof and to address the driver's behavior as a result. The driver was terminated "with cause" as a result clearing the purveyor and navigating the delivery service from further future liability.

In a fourth example, Dan and Trish fall on hard times when Dan loses his job still really want the new Madden NFL 20 Superstar Edition video game. They decide to order the game online. The order is placed in the locker on their front porch. They retrieve the order when they get home. The delivery, itself, 'and' photographs and/or video of Trish grabbing the package out of the locker at 2:08 AM, the data surrounding the delivery, such as records of who delivered the item, what time it was delivered, and what the parcel containing the video game weighed are all on record. The next day, Dan, not considering that the detailed records associated with the delivery and retrieval are available, gives the game to his son for his birthday and has Trish telephone the purveyor to act as if the order never got there. After a few days, Dan goes online to the purveyor's website and launches a complaint about having placed an order that he never received. The purveyor, taking this matter very seriously, obviously having visual, weight, time and date information regarding Dan and Trish's claim immediately declines and refuses to dispatch another, expensive replacement, Madden NFL 20 Superstar Edition video game to Dan and Trish. The customer, in this case, Dan and Trish, attempted to unjustly enrich themselves through deceitful representation of the duly completed delivery, a/k/a Customer Piracy, at the good-hearted expense of the large purveyor's willingness to take their word for it. In this case, the purveyor, who is typically worried about its reputation and who is normally ready to immediately re-send the order to take care of their customer's needs, has been able to save themselves the cost of the item plus the expenses associated with delivering it to Dan's house a second time based on false pretenses. The locker saves the purveyor over $100 and allows them to answer Dan's attack online with factual data that dispels his erroneous claim and, moreover, permits the purveyor to assess making future deliveries to this customer.

In the case of the delivery of perishables (like food and other grocery store items that may require cooling or warming from a grocer or purveyor of same), in order to lessen the risk of food or other spoilage from overheating or freezing, as the case may be, while the items are awaiting retrieval from the intended recipient and are stored in the locker, internal compartment(s) 5, 8, 9 and 27 of the locker may be designed to be climate-controlled using either thermoelectric technologies 9 to heat and/or cool the interior of the locker to the degree permissible by the environs and temperatures then present and relative to its location, or in other embodiments, may use or deploy more conventional cooling, like, compressor-based refrigeration devices 9 and/or other heat-exchanging cooling or warming mechanisms in cavities 5, 8 and/or 9 to provide warming functions and/or other space heating/warming alternatives for cooling or heating the interior of the locker to create and maintain an environment inside the container that might preserve the contents for limited periods of time. Battery back-up system 9 and 19 may serve as a battery back-up system to energize heating and cooling systems maintaining the temperatures desired in cavity 5 while perishables are being stored therein among other systems, functions, appliances and devices on-board.

In some embodiments, the locker may be used as an alternative form of temperature-controlled container, like a cooler, portable refrigerator or a warming box for limited and typically temporary purposes and periods of time. As such, the locker in its portable form may be utilized as a highly portable and mobile form of refrigeration or heating/warming device for beverages, foods, medicines and the like, wherein it can easily be used as such for the purposes of providing cooled or heated space for the stowing of food items, medicines, and other things of importance to the user in outdoor and indoor, electrified or off-the-grid location and situations such as backyards around the pool, picnics, bar-b-ques, grilling out events, camping, hunting, tailgating, parties in remote areas and the like, the device, being wheeled, portable, battery-charging, battery and house-powered or otherwise able to be powered through other like-voltage power sources (vehicles, etc.) through power cords 24, may be used to cool or heat items by being connected to an electrical mains source through its cord and plug 24, using its on-board battery 27 as a power source with access thereto through the battery-well hatch 20A, plugging it into another low-voltage power source, such as a car or truck battery through direct-connect or alternative means such as through a cigarette lighter installed in the car, truck, tractor or other device through its 12 VDC connector port 26. When connected to an alternative source of power for operation, the apparatuses' on-board batteries 27 are also trickle-charged through a charging system located in cavity 9 in order to re-charge the on-board batteries using a common trickle-charging converter with automatic shut-off 27 once fully charged to protect the batteries and system of both the source and the apparatus itself.

Ultraviolet germicidal irradiation (UVGI) is a disinfection method that uses short-wavelength ultraviolet (ultraviolet C or UV-C) light to kill or inactivate microorganisms by destroying nucleic acids and disrupting their DNA, leaving them unable to perform vital cellular functions. UVGI is used in a variety of applications, such as food, air, and water purification. Maintaining a clean atmosphere inside the container locker may be important to, generally, prevent the spread of illness when UVGI devices are utilized to produce strong enough UV-C light in circulating air or water systems to make them inhospitable environments to microorganisms such as bacteria, viruses, molds, and other pathogens on the surfaces where their UV light is shed.

In embodiments of the present disclosure, given its designed enclosed dark cavity as the main depository area for parcels, cartons and items being delivered, this UVGI process inside the locker, such as in cavity 5, and/or inside prescription pocket 27 (RxPocket™) can reduce risk of the spread of disease, such as COVID-19, as well as other touch-borne diseases (influenza, cold germs, and the like) as packages are touched by people and are passed along in delivery processes.

In some embodiments of the present disclosure, the container locker may contain at least one, and even an array of, UVGI devices wherein the UV light may be shed on the parcels contained in the locker while such parcel(s) wait to be retrieved by the recipient thereof. The UVGI lighting/device or array of devices may be automatically triggered to shed their UV light on the parcels or items placed in the container locker through the on-board computer or cellular systems when the top lid is closed and re-locked after a delivery has been made as a layer of germicidal sterilization and disinfection (irradiation) of those parcels and items placed in the locker. For those familiar with the art, other disinfection forms of protection for the user may be utilized with or in lieu of UVGI technologies as well in the containment areas of the locker.

Americans spend nearly $10 billion on delivered-to-the-door pizza, alone, every single year. In fact, according to statista.com, "consumer spending on food delivery in 2015 was worth around 30 billion U.S. dollars—four billion U.S. dollars of this was accounted for by online delivery sales. Delivery services are a popular dining option with U.S. consumers, as a November 2016 survey found that 20 percent of respondents use food delivery at least once a week." In fact, during the Covid-19 pandemic of 2020 when restaurants across the land were forced to close because of social distancing requirements, take-out and delivery were the only means through which one might patronize a restaurant. In times such as these, the container locker becomes even more useful and important to the masses by providing additional convenience to Americans and others around the globe in having a safe, secured and environmentally controlled location to make these types of deliveries in their absence at the door. Given the automatic capabilities to receive orders in the absence of its owner/recipient, and in some embodiments, to heat or cool the contents placed in cavity 5 until conveniently retrieved by the owner/receiver from the locker's temperature-controlled cavity 5, it is uniquely suited for the temporary placement and storage of food/take-out orders being delivered from restaurants to be held until the recipient is able to or otherwise desires to retrieve same. In consideration of the time constraints that many in the world find themselves undergoing in today's hustle-bustle never-slow-down times, the locker may provide a well-suited and secure receptacle to receive a take-out-delivery order delivered by a local or regional restaurant when the intended recipient is not at the location, is unavailable and/or is unwilling to greet the delivery person, UAV, drone, manned, unmanned or other delivery means. Regardless when the order is placed, the goods to be delivered may be sent out to the intended recipient when readied and the locker performs the duty of secure, confirmed reception and climate-controlled holding of the ordered goods, in this case, food, as the intended recipient is away from the location navigating her/himself home from work or is accomplishing other tasks like picking up their children, running to the drugstore or checking on or caring for their senior parent, etc. In practical terms, and based upon the terms of the restaurant and the purchaser/recipient, a food order can be placed by the busiest of the busy and can be prepared, delivered, placed into the locker's climate-controlled environment and held temporarily without spoilage until the receiver removes it from the locker.

Those having skill in the art will recognize that examples of such other devices and/or processes and/or systems might include—as appropriate to context and application—all or part of devices and/or processes and/or systems of (a) an air conveyance (e.g., an unmanned aerial vehicle or drone, an airplane, rocket, helicopter, etc.), (b) a ground conveyance (e.g., an automated delivery device or machine, car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., a delivery or retrieval services company, an Internet Service Provider (ISP) entity such as AT&T, Verizon, T-Mobile, Comcast Cable, Qwest, Southwestern Bell, etc.), or (g) a wired/wireless services entity (e.g., AT&T, Verizon, Sprint, Cingular, Nextel, etc.), etc.

Those skilled in the art will appreciate that a delivery and a pickup as used herein, both, anticipate the requirement of gaining controlled access into the locker interior through the use of its systems for the purposes of delivering (i.e., delivery) and/or retrieving (i.e., pickup or retrieving) items, either placing them into the locker (when delivering) or retrieving them from (when picking up) and that the item's placement thereinto are conceived as a temporary placement, for a specific purpose and convenient time for the subject users.

In conclusion, embodiments of the present disclosure may provide a means for users to de-risk, record and confirm and secure the material aspects of the delivery (or pick-up) equation related to the processes of delivering goods and merchandise and/or returning them to the original sender of same, especially when using third-party personnel or services or automated means to perform these tasks. Packages can be secured in a locker that prevents the package's ability to be stolen, freeing consumer's minds and more of their discretionary dollars to use this form of delivery. The container locker may use on-board electronic scale and digital load-cell system to weigh items as they are received into or removed from the container locker. Their weight(s) are tabulated, and this confirming weight information/data may be dispatched to parties interested in the delivery or retrieval along with the UPC information. The user may verify weight coming into the container locker and specific weight data for items being held for pickup in the container locker. This information may allow for the tracking of multiple items being placed into or taken from the container locker. Embodiments of the present disclosure may be wheeled, highly portable and easily relocatable and, generally sized to be brought indoors through a common sized doorway if desired. They can easily be ganged or collocated in groups of multiple or many individual units that are permanently affixed (bolted) to its permanent location in a communal secured group facility or area in residential and commercial types of settings. The container locker may utilize soft rubberized wheels or wheel covers to protect interior floor surfaces when rolled into an interior space such as a home. On-board batteries and low-voltage power systems may be re-charged using other AC and/or DC power alternative sources and can be plugged into common 60 Hz/120 v house power to charge the on-board batteries with the connection through a retractable or non-retractable power cord allowing the locker to connect to other power sources wherein the batteries may be charged, bypassed altogether, or both. The container locker may be connected to other power sources in varied AC and DC voltage ranges to operate, charge onboard systems or both simultaneously or independently of each other and may use a solar collector(s) to harvest solar power to operate its on-board systems or to charge its on-board batteries or both simultaneously or independent of each other. The container locker may include an automated lid (or top) that may be activated via different human-entered or wirelessly invoked stimuli which can open, close and lock with or without the aid of a person and can receive or hold for delivery items that may be delivered or retrieved by manned or un-manned means or modes such as drone-drop or cargo-carrying robot delivery or retrieval. The container locker may utilize a cushioned or padded floor system to cushion the fall of items into it in order to prevent items being dropped into it from breakage or damage which is especially important in un-manned delivery events. On-board antennas, wire connectivity and or other connectivity may be provided, allowing the systems to be able to be quickly and easily connected to, and integrated temporarily or permanently with a litany of other systems, cellular phones, etc. to provide utility through its on-board computer, electronic and digital systems to connect in a hard-wired, wireless, cellular, IoT and other protocol formats of communication and interoperability. Items may be refrigerated or warmed to maintain ambient temperatures inside its main cavities to prevent spoilage of items delivered or items staged there for retrieval. Motion can be detected around the container locker or in front of it through the use of motion sensors to wake sleeping systems, alert others through interconnected communications, and perform other functions related to activity proximate the locker. A microphone may be embedded in its surface areas to permit delivery personnel (or others) to communicate verbally through the devices on-board, interconnected or uplinked networks, and motion and other sensors, computers, devices and appliances on-board and as connected and used through other remote connected systems may be provided for security, mobility, communications, cooling and warming, interconnectivity and other forms of capacity and utility to interactivity interact with people, machines, and other things therethrough. The container locker can scan, photograph or video areas around it and the inside of its main cavities and can store or forward this visual data to others to visually verify and visually confirm deliveries or retrievals. The container locker may store and/or forward data gathered through scanning to interested parties such as for security and/or notification. The container locker may be GPS-locatable and have the ability to transmit alarm data to other locations signalizing to users, law enforcement, or others that it has been removed from its intended location and to pinpoint its then current location. The container locker can be physically relocated by its remotely located owner/user through computer or cellular phone connections to physically drive it, or move it, from one location to another via a software application (an App), the driver being situated in a remote location and desiring, for example, bring it indoors, into a garage and/or relocate it to a less conspicuous location chosen by the owner/user after a delivery or retrieval has been made. When alarmed or in a configured alarm state, the container locker can employ its varied forms of exterior lighting, cameras, sounders or speakers and peripherals to indicate and alert audibly or visually to others that it has been breached, is being or has been stolen or is otherwise at risk. The container locker may interconnect with other access restrictive features, such as digitally/electronically controlled locked gates, locked doors and other access restrictors to provide manned and unmanned delivery or retrieval personnel or machines to gain access to areas proximate the locker so that they might perform their delivery or retrieval duties at the locker's location. There may be automatic interior lighting to shed light in one or more of its containment cavities when such cavities are opened for access by the user and to assist him/her in loading deliveries or when retrieving parcels or items from it. Exterior lighting packages may be built into the exterior surface areas used for security and ambient lighting purposes. The container locker can utilize a designed docking station that further hinders the locker from being relocated from its intended location and which may permanently adhere it to a structure to address insurance issues that may arise regarding its use and being covered under insurance policies. The container locker may include a tether or retractable tether location-locking system to secure it to immovable objects like a pole or a house making it exceedingly difficult for a would-be thief to steal the locker and its contents from its intended location. The locker may use a highly reflective material embedded in the plastics materials used in the manufacture of the exterior shell or which is placed on the exterior aspects that permit it to be readily and easily seen and locatable in vehicle headlights in dark and darkening environments. A glow-in-the-dark material may be embedded in the plastics materials used in the manufacture of the shell exterior to permit it to be charged with sunlight and highly visible in dark or darkening settings. Waterproof or other forms of exterior sound-speakers housed in the shell structure may provide audible sound and music through its own computer system and wireless or hard-wired connections. Waterproof exterior speakers may be housed in the shell to connect using USB connected devices and/or other wirelessly connected devices and systems connected to the locker to play music and/or to broadcast sound. The container locker may provide a plug-in extension point for extension cords or other devices or appliances that draw on 60 Hz/120 v common house power to operate. When connected, integrated and communicative with the sender's or deliverer's barcode or other label or tracking systems, the locker's computers, systems and optics can seamlessly recognize a parcel or items on the parcel or item label (as scanned) and communicate this data to others quickly. Thus, embodiments of the present disclosure may decrease issues related to (i) Porch Piracy prevention, (ii) Delivery Personnel Piracy prevention and (iii) Customer Piracy prevention, all forms of theft in the delivery processes, being a unique and useful tool for the sender, the delivery personnel or drone and the intended receiver of a parcel or item, through the use of its automatic or manual locking sealed lid system, on-board scale(s) cameras and peripherals and its ability to photograph and communicate with others to verify and confirm that the placement of a parcel was made or a parcel was retrieved in or from, respectively, one of its cavities.

Certain embodiments of the present disclosure may provide radio frequency identification (RFID) and/or smart label system(s) and technology to assist companies in tracking their assets into, out of or proximate the present disclosure. RFID may provide a wireless, non-contact use of electromagnetic or electrostatic coupling in a radio frequency form in a part of the electromagnetic spectrum to transfer data and uniquely identify objects, animals, and/or humans or anything to which the RFID tag is affixed. An RFID tag may verify an asset's release from an origin and its arrival at a destination.

An RFID system may include three primary components: a scanning antenna, a transceiver, and a transponder. With transponder capabilities, using GPS and other means, the sender and the receiver may know where the parcel is along its path from origin to destination. RFID tags may be attached to a parcel or the items inside of a parcel to transmit stored data to the system's antenna. When the scanning antenna and transceiver are combined, they may be referred to as an RFID reader or interrogator. An RFID reader is a network-connected device that can be portable (i.e., a mobile reader) or permanently attached (i.e., a fixed reader). It uses radio waves to transmit signals that activate the tag. The antenna may receive the stored data from the tag and transmit that data to an RFID reader. The reader, which may be connected to the antenna wirelessly, may receive the data from the RFID tag, and that data can be transmitted wirelessly and/or in hardwired form into an RFID database where it can be stored, sent along to other interested parties and evaluated. Once activated, the tag may send a wave back to the antenna, where it may be translated into data and then forwarded to others needing this data through a communication system. This data can signal that a specific parcel or package is at a specific location at a specific time and is transmissible via cellular and or other communicative means to interested parties much like when a driver/delivery person scans the label on a delivered parcel conventionally at its destination. Reducing scanning may be key to operating cost savings, particularly where there may be little-to-no human interaction (like drone or other robotic deliveries) may be involved in the delivery of something.

There are three main types of RFID systems: low frequency (LF), high frequency (HF) and ultra-high frequency (UHF). Low-frequency (LF) RFID systems may range from 30 KHz to 500 KHz, though the typical frequency may be 125 KHz. LF RFID has short transmission ranges, generally anywhere from a few inches to less than six feet. High-frequency RFID systems may range from 3 MHz to 30 MHz, with the typical HF frequency being 13.56 MHz. The standard range may be anywhere from a few inches to several feet. UHF RFID systems may range from 300 MHz to 960 MHz, with the typical frequency of 433 MHz and can generally be read from 25-plus feet away. Microwave RFID systems also may be available. These may run at 2.45 Ghz and can be read from 30-plus feet away. Frequencies vary greatly by country and region. Any of these frequencies may be utilized without departing from the present disclosure.

There are two main types of RFID tags: active and passive. An active RFID tag has its own power source, often a battery. A passive RFID tag may receive its power from the reading antenna, whose electromagnetic wave induces a current in the RFID tag's antenna. Embodiments of the present disclosure may provide systems that may be outfitted with either or both simultaneously. Smart labels may be considered simple RFID tags. These labels may have an RFID tag embedded into an adhesive label and feature a barcode. They can also be used by both RFID and barcode readers. Smart labels can be printed on-demand using desktop printers, where RFID tags require more advanced equipment. Like RFID tags, smart labels, also called smart tags, may utilize an extremely flat configured transponder under a conventional print-coded label, which may include a chip, antenna, and bonding wires as an inlay. The labels, which may be made of paper, fabric, or plastics, may be prepared as a paper roll with the inlays laminated between the rolled carrier and the label media for use in specially designed printer units.

RFID and/or smart tags may be utilized for both manned and unmanned deliveries and retrievals in embodiments of the present disclosure. Parcels, assets, items and, even, people can be tagged with an RFID tag. For example, an RFID tag may be affixed or otherwise embedded into the parcel, asset, and/or item. When an item is tagged with an RFID tag or smart tag, users may automatically and uniquely identify and track that tagged item as it moves and/or is utilized throughout its meandering and/or use in an enterprise and on to a customer. This auto-ID technology may allow tags to be read without line of sight and, depending on the type of RFID tag and system being used, may have a read range of anywhere between a few inches to over 20 meters.

RFID tags in conjunction with transponder(s) and/or reader(s) may be used to permit companies to track their assets, which may include but are not limited to vehicles, machinery, and/or parcels. These assets (tagged with RFID tags/smart labels) may be tracked as they move about, through an enterprise, and out of the enterprise's scope of purview or control and into and through distribution and transit channels to a specified destination. Using RFID and smart labels with a parcel can de-risk the logistical and distribution loss aspects of delivery and can assist by confirming delivery in that last mile and at the endpoint of the shipping process.

Use of RFID and/or smart labels may shave costs of production and/or delivery and improve efficiency in the delivery process. For example, use of RFID tags may eliminate (or at least reduce) manual scans for locational and delivery data for deliveries of parcels at the intended destination. Parcels may have RFID embedded in the parcels themselves for tracking and receipt verification at the destination with the proper reader to log placing an item into or taking it out of the container locker with this system. RFID also may be used in the goods return process where a good is picked up, the buyer's account credited, and the good being automatically logged back into inventory at the purveyor's distribution center or warehouse immediately upon pickup at its location in an automated way. This capability may be placed at the front or back door of every location that utilizes it for the receipt of deliveries. By including at every destination point, the processes of tracking to destination and confirmation of receipt may be more efficient, especially for online merchants like Amazon who delivered an estimated 7.7 billion packages (in 2021).

Embodiments of the present disclosure may provide a communicative landing point location to scan/read the RFID tags/smart labels and send appropriate data back to the origin or to other parties to confirm that delivery has, in fact, occurred at the time when delivery or pickup occurs. When deployed with the appropriate reader panels inside of the Total-Vault™ device in package logistics, there may be an abundance of useful data that can be transmitted back to a variety of enterprises interested in the successful delivery or retrieval of a specific shipment, especially if that shipment is date sensitive. It can be tremendously useful to have the means to follow a package from its origin (i.e., a distribution center or a store) to its destination (a delivery point) using this tracking technology, and embodiments of the present disclosure may provide a capable end-point confirmation to verify the accomplishment of a successful delivery and transmit data to others to signal that the shipping task is completed.

Systems according to embodiments of the present disclosure may be outfitted with one or more of the types of RFID systems for its operation. The RFID system may be powered by the onboard power delivery systems elsewhere discussed and depicted herein. The RFID system may be integrated with other onboard systems, like communication systems, antennas, camera, weighing and or other systems described herein.

Figure 10A:
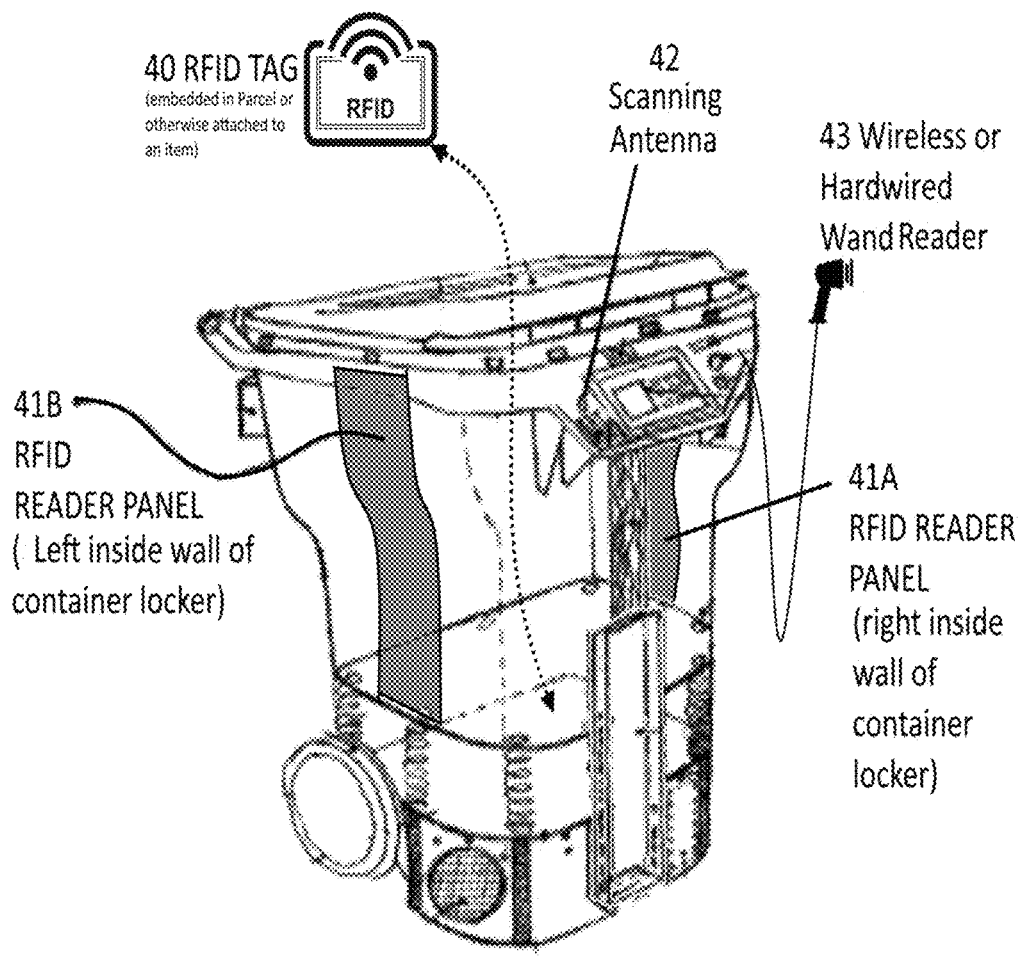
FIG. 10A depicts a container locker incorporating RFID according to an embodiment of the present disclosure.

FIG. 10A depicts a container locker incorporating RFID according to an embodiment of the present disclosure. The container locker according to an embodiment of the present disclosure may include scanning antenna 42, RFID reader panels 41A and 41B, wireless or hard-wired smart-label reader wand 43 which may be integrated into other onboard computers and communication systems previously described herein. It should be appreciated that the RFID system may be operated in, on and/or proximate the container locker in embodiments of the present disclosure. In addition, there may be an externally attached or permanently connected RFID and/or camera wand 43 to read labels or tags 40 as parcels and items are identified by the system as they are placed into the cavity(ies) and/or to read RFID and or smart-label tags associated with the parcels or items so placed. Wand 43 may be attached to onboard systems via wireless or hard-wired means and/or may be integrated in the onboard systems as an extension in embodiments of the present disclosure. Wand 43 may provide for scanning upon delivery of smart labels, universal product codes (UPC labels), and/or RFID tags. The data scanned may be communicated to interested parties regarding the delivery or return pickup without the delivery personnel carrying a separate scanning device. Other on-board camera systems and/or digital and/or computer systems may also be utilized in addition to the above to provide marginal identification efficacy and may also play a part in reading and confirming bar-code and other forms of labeling.

FIG. 10A depicts one way that an RFID system can be installed in and on the container locker and its main receiving cavity to read data from the RFID tags in or on items or parcels as they are loaded into or taken out of the container locker. Side-wall readers, working in parallel, may be installed on opposing sides of the cavity where parcels are placed and read within the container locker. A similar, but smaller version of this general type of RFID installation may also be installed on inside opposing sidewalls of RX pocket cavity 27 to identify and verify prescription drug or other controlled substance or highly secured identification and delivery needs. As parcels tagged with RFID tags are lowered into the container locker or placed into RX pocket 27, RFID readers 41A and 41B, coupled with the antenna and onboard power and communication systems, read, identify, and communicate data about the item and by doing so verify that the item was delivered to the appropriate location. Onboard communication systems can relay this delivery data to interested parties.

It should be appreciated that the described delivery functions described herein would, in reverse, provide additional efficacy to a merchant or delivery personnel when a product return is effected and a parcel or item is picked up by a delivery person to return to its origin (a return). In the case of a return, the RFID system via onboard communication systems can assist the merchant or purveyor in recognizing and qualifying that the item has been picked up and, resultantly, may be automatically placed the item(s) immediately back into its inventory ledger making the item(s) available for sale to others.

Figure 10B:
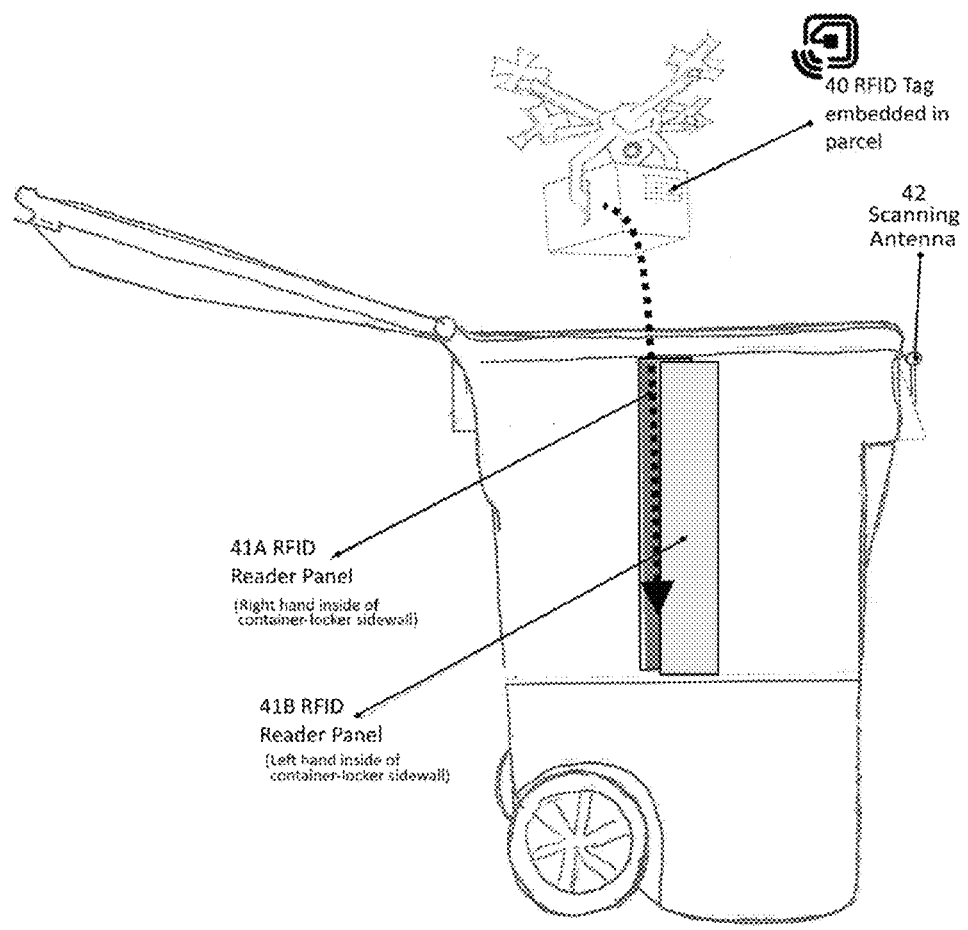
FIG. 10B depicts a container locker incorporating RFID in connection with an aerial drone according to an embodiment of the present disclosure.

As contemplated herein, when it comes to aerial drone or other non-human unmanned types of deliveries or return pickups, such as depicted in FIG. 10B, the onboard RFID system according to embodiments of the present disclosure can provide tremendous marginal efficacy to the drone-delivery formula and processes with the use of this RFID-equipped container locker and its systems. If a parcel being carried by a drone is fitted with RFID tag 40 from the sender or delivery company, RFID panels 41A, 41B either embedded into or otherwise affixed to the wall(s) and/or one that is packed inside the box with the packaged items, can read tag 40 and communicate the received data to interested parties with or without other data (photographs and other data).

In short, using RFID technology according to embodiments of the present disclosure can personalize and customize the process for every merchant, retailer, or delivery enterprise. Every company has its own desired data format that it maximizes for its own efficiency. That is, in shipping goods to consumers, there is not a one-size fits all hat for the shipper/seller when it comes to the specifics of the data that they particularly gauge or monitor to integrate with their own proprietary accounting, tracking and supply-chain metrics. Each maker or merchant measures their success or failure, especially in the last mile. With an RFID-capable endpoint according to embodiments of the present disclosure, these indigenous metrics from company to company can all use the same endpoint but can measure the activity with their own inherent established metrics embedded in their own RFID tag or smart tag. Tailoring this endpoint (delivery and/or retrieval) of an item may involve merely dropping the sender's own RFID tag in the parcel, bag or container as it leaves their distribution center, warehouse, or store. At the endpoint, the successful delivery or retrieval can wirelessly return the specific type of data that the individual sender thereof wants for their effort to measure, confirm, and otherwise analyze the delivery process. The data returned may already be in a format and layout and type that is germane to their own proprietary internal system(s) for their specific enterprise because that specific enterprise may have programmed the RFID tag, smart label or other readable UPC or the like at its shipment origin. Embodiments of the present disclosure, with its RFID and communication system can the type and amount(s) of data that may be meaningful for the seller/merchant/delivery enterprise, all accessing the TotalVault™ for their enterprise almost as though it was built for them as a natural system embedded extension of their already well laid-out delivery system.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A container locker comprising:
   a first cavity that accepts or holds one or more parcels having a radio frequency identification (RFID) tag;
   a second cavity positioned below the first cavity, the second cavity having a ceiling that provides a cushioned surface for the first cavity to receive the one or more parcels;
   a third cavity that houses mechanical and electrical equipment for operation of the container locker;
   at least one RFID panel disposed within a wall of the container locker that reads data on the RFID tag of the one or more parcels; and
   a lockable lid that removably covers the first cavity.

2. The container locker of claim 1 further comprising:
   a scanning antenna.

3. The container locker of claim 1 further comprising:
   a reader wand capable of reading an RFID label or smart tag as one or more parcels are placed into the first cavity.

4. The container locker of claim 3, wherein the reader wand is wireless or hard-wired and is integrated into the mechanical and electrical equipment in the third cavity.

5. The container locker of claim 3, wherein the reader wand is externally attached to the container locker.

6. The container locker of claim 1, wherein the at least one radio frequency identification (RFID) panel are two RFID panels installed on opposite sides of the first cavity.

7. The container locker of claim 1 further comprising:
   a prescription pocket that is locked and accessible through one or more access points to the container locker or separate independent outside areas of the container locker.

8. The container locker of claim 7, wherein the prescription pocket is interiorly secured within the first cavity and independently accessible from an independent sidewall hatch or locking opening.

9. The container locker of claim 7, the prescription pocket having at least one RFID panel on opposing sidewalls of the prescription pocket, wherein the at least one RFID panel reads data on the RFID tag associated with the parcel placed in the prescription pocket.

10. The container locker of claim 1, the second cavity further comprising:
    a drop-cushion spring system positioned below the ceiling.

11. The container locker of claim 1, wherein the mechanical and electrical equipment in the interior or exterior of the container locker comprises one or more of the following:
    refrigeration equipment, heating/warming equipment, cellular phones and related cellular technology communication and interface devices, on-board single board computers and other computers and interface devices, 4G, 5G (and future versions of these protocols) repeater(s) or relay modules to complete 4G 5G (including contemplated future versions thereof) networks and communication systems, interior and exterior cameras, scanners and optical devices, USB and other computer interface connection ports, Wi-Fi repeaters and boosters, antennas and transmitter and transceiving devices, communication and uplink modules, equipment and devices, electrical cords and plugs and related powering and charging equipment, batteries, battery-well access hatches and locks, security cords, power cords, gyroscopic devices, motion sensors, speakers, horns, piezoelectric sounders, interior or exterior lighting, LED-type ambient, emergency and security lights and lighting equipment, ancillary jumper-duplex outlets, mobility and lid opening motors, gearing, gear boxes and related belts, chains and sprockets, and autonomous movement gearing or sprockets, axles and or wheels, knock-out penetrations, scale equipment, and scale-related electronics and equipment.

12. The container locker of claim 1, wherein the lid operates as a manual lid, an automated tip-lid, or slide-lid for the first cavity through interaction with one or more on-board systems that perform opening, closing, unlocking, and locking functions.

13. The container locker of claim 1 further comprising:
an insulative sleeve on a sidewall, the lockable lid and/or floor areas of the container locker to control temperatures inside of the container locker.

14. The container locker of claim 1 further comprising:
at least one interior camera that takes photographs and/or video of the at least one parcel inside the first cavity, wherein the photographs, related data, and/or video are transmitted to at least a sender, a recipient and/or a deliverer of the at least one parcel to confirm that the at least one parcel is verifiably secured in the container locker or has been retrieved from the container locker and at least one exterior camera that takes photographs and/or video of exterior areas proximate the container locker wherein the photographs, related data, and/or video are similarly transmitted to at least a sender, a recipient and/or a deliverer of the at least one parcel to confirm that the at least one parcel is verifiably secured in the container locker or has been retrieved from the container locker.

15. The container locker of claim 1 further comprising:
a solar collector positioned on top of the lid, wherein the solar collector collects heat and converts into electricity to charge on-board batteries, operate the container locker, and/or charge devices connected to the container locker.

16. The container locker of claim 1, wherein the lid opens to provide an unobstructed opening for manned or unmanned aerial or robotic delivery or retrieval of at the least one parcel from the first cavity.

17. The container locker of claim 1 further comprising:
a retractable or other type of security tether that connects the container locker to an immovable object to secure the container locker in place and prevent theft.

18. The container locker of claim 1 further comprising:
one or more computerized GPS devices, cameras and motion sensors configured to generate one or more shut audio or visual alerts indicating a breach or attempted breach of the container locker.

19. The container locker of claim 1 further comprising:
circuitry, antennas, and related equipment configured for generating transmission of one or more wireless or cellular signals to provide connectivity to local wireless or cellular communication systems to provide, repeat, and boost signals to and to provide locational information of the container locker.

20. The container locker of claim 1 further comprising:
at least one on-board ultraviolet germicidal irradiation (UVGI) device or alternative sterilization system to sterilize contents placed into the container locker to sanitize contents, prevent the transmission of contagious diseases, and/or to clean and to prevent the spoilage of contents of the at least one parcel when placed in the container locker.

* * * * *